United States Patent [19]

Matusik

[11] Patent Number: 5,783,681
[45] Date of Patent: Jul. 21, 1998

[54] ANDROGEN REGULATION WITH DNA SEQUENCES OF RAT PROBASIN GENE

[75] Inventor: Robert J. Matusik, Winnipeg, Canada

[73] Assignee: University of Manitoba, Winnipeg

[21] Appl. No.: 351,365

[22] PCT Filed: Aug. 9, 1993

[86] PCT No.: PCT/CA93/00319

§ 371 Date: Mar. 8, 1995

§ 102(e) Date: Mar. 8, 1995

[87] PCT Pub. No.: WO94/03594

PCT Pub. Date: Feb. 17, 1994

[30] Foreign Application Priority Data

Aug. 7, 1992 [GB] United Kingdom ............... 9216851

[51] Int. Cl.$^6$ .......................... C07H 21/04; C12N 15/00
[52] U.S. Cl. ...................... 536/24.1; 800/2; 800/DIG. 1; 514/44; 435/172.3
[58] Field of Search ................. 424/93.1; 435/240.2, 435/172.3; 514/44; 800/2, DIG. 1–4; 536/23.1, 23.5

[56] References Cited

U.S. PATENT DOCUMENTS

| | | | |
|---|---|---|---|
| 5,162,215 | 11/1992 | Bosselman et al. | 435/172.3 |
| 5,175,383 | 12/1992 | Leder et al. | 800/2 |
| 5,545,808 | 8/1996 | Hew et al. | 800/2 |

FOREIGN PATENT DOCUMENTS

WO 90/09443  8/1990  WIPO .

OTHER PUBLICATIONS

Pursel et al, Genetic Engineering of Livestock. Science vol. 244 pp. 1281–1288. Jun. 16, 1989.
NIH Panel, Report and Recommendations of the Panel to assess the NIH Investment in Research on Gene Therapy, Dec. 7, 1995.
Verkerk et al, Identification of a Gene (FMR–1) Containing a CGG Repeat Coincident with a Breakpoint Cluster Region Exhibiting Length Variation in Fragile X Syndrome. Cell vol. 65, pp. 905–914, May 31, 1991.
Perry et al, The Surface Envelope Protein Gene Region of Equine Infectious Anemia Virus is not an Important Determinant of Tropism In Vitro, J. Virol. vol. 66 No. 7 pp. 4085–4097, Jul. 1992.
Adams, J.M., Harris, A.W., Pikert, C.A., et al. Nature 318:533, 1985.
Adler, A.J., Scheller, A., Hoffmann, Y. and Robins, D.M. Molecular Endocrinology 5:1587, 1991.
Adler, A.J., Danielsen, M. and Robins, D.M. Proceedings of the National Academy of Sciences of the United States of America 89:11660, 1992.
Allan, G.F., Tsai, S.Y., O'Malley, B.W. and Tsai, M.J. Bioessays 13:73, 1991.
Allison, J., Zhang, Y.L. and Parker, M.G. Molecular & Cellular Biology 9:2254, 1989.
Anderson, W.F. Science 256:808, 1992.
Anonymous, Immunol Ser; 41:1–396 1988.
Anonymous, Workshop on Neoplastic Transformation in Human Cell Systems In Vitro: Mechanisms of Carcinogenesis. Apr. 25–26, 1991.
Anonymous, Raven Press Ser Mol Cell Biol; 1:1–364 1992.
Armbruster, D.A. Clin Chem 39:181, 1993.
Bautch, V.L. Molecular Biology & Medicine 6:309, 1989.
Beato, M. Cell 56:335, 1989.
Bookstein, R. and Alfred, D.C. Cancer 71:1179, 1993.
Borrelli, E., Sawchenk, P.E. and Evans, R.M. Proceedings of the National Academy of Sciences of the United States of America 89:2764, 1992.
Bouchard, L., Lamarre, L., Tremblay, P.J. and Jolicoeur, P. Cell 57:931, 1989.
Breuer, M., Slebos, R., Verbeek, S., van Lohuizen, M., Wientjens, E. and Berns, A. Nature 340:61, 1989.
Brinkman, A.O., Kuiper, G.G., Ris–Stalpers, C., et al. Journal of Steroid Biochemistry & Molecular Biology 40:349, 1991.
Brinkman, A.O., Jenster, G., Kuiper, G.G., et al. Journal of Steroid Biochemistry & Molecular Biology 41:361, 1992a.
Brinkman, A.O. and Trapman, J. Cancer Surveys 14:95, 1992b.
Burck, K.B., Liu, E.T. and Larrick, J.W. Oncogenes: An Introduction to the Concept of Cancer of Cancer Genes. New York, Springer, 300 p., 1988.
Butel, J.S., Sepulveda, A.R., Finegold, M.J. and Woo, S.L. Intervirology 31:85, 1990.
Buttyan, R. and Slawin, K. Cancer & Metastasis Reviews 12:11, 1993.
Callahan, R. and Campbell, G. Journal of the National Cancer Institute 81:1780, 1989.
Carter, B.S., Epstein, J.I. and Isaacs, W.B. Cancer Research 50:6830, 1990a.
Carter, B.S., Ewing, C.M., Ward, W.S., et al. Proceedings of the National Academy of Sciences of the United States of America 87:8751, 1990b.

(List continued on next page.)

*Primary Examiner*—Jasemine C. Chambers
*Assistant Examiner*—Deborah J. R. Clark
*Attorney, Agent, or Firm*—Sim & McBurney

[57] ABSTRACT

A DNA sequence (–426 to +28 base pairs) cloned from the probasin (PB) gene promoter region confers androgen regulation in cell culture and prostate specific expression in transgenic non-human eukaryotic animals. Various PB promoter fragments impart preferential regulation by androgens compared to other steroid hormones on fused transgenes. Alteration of the DNA sequences and/or combinations permits production of an (1) assay for androgenic or anti-androgenic materials, (2) transgenic non-human eukaryotic animal models for prostatic disease, (3) cell culture models for prostatic disease, and (4) treatment of human benign prostatic hyperplasia and human prostate cancer by gene therapy. This invention permits assays on agonist and antagonist of the androgen receptor or pathways that result in androgen action, testing materials for carcinogenicity of the prostate, testing drugs and gene therapy, or protection potential of materials on prostatic cells against prostatic disease.

17 Claims, 5 Drawing Sheets

OTHER PUBLICATIONS

Cato, A.C.B., Henderson, D. and Ponta, H. Embo Journal 6:363, 1987.

Cattini, P.A., Peritz, L.N., Anderson, T.R., Baxter, J.D. and Eberhardt, N.L. DNA 5:503, 1986.

Claessens, F., Celis, L., Peeters, B., Heyns, W., Verhoeven, G. and Rombauts, W. Biochemical & Biophysical Research Communications 164:833, 1989a.

Claessens F., Dirckx, L. Delaey, B., et al. Journal of Molecular Endocrinology 3:93, 1989b.

Claessens F., Rushmere, N., Celis, L., Peeters, B., Davies, P. and Rombauts, W. Biochemical Society Transactions 18:561, 1990a.

Claessens, F., Rushmere, N.K., Davies, P., Celis, L., Peeters, B. and Rombauts, W.A. Molecular & Cellular Endocrinology 74:203, 1990b.

Claessens, F., Celis, L., De Vos, P., et al. Biochemical & Biophysical Research Communications 191:688, 1993.

Culotta, E. Science 260:914, 1993.

Sorrentino, et al. Science 257:99, 1992.

Dalemans, W., Perraud, F., Le Meur, M., Gerlinger, P., Courney, M. and Pavirani, A. Biologicals 18:191, 1990.

Darbre, P., Page, M. and King, R.J.B. Molecular & Cellular Biochemistry 6:2847, 1986.

Davies K. Nature 361:5, 1993.

De Bellis, A., Quigley, C.A., Cariello, N.F., et al. Molecular Endocrinology 6:1909, 1992.

De Vos, P., Claessens, F., Winderickx, J., et al. Journal of Biological Chemistry 266:3439, 1991.

De Wet, J.R., Wood K.V., Deluca, M. and Helinski, D.R. Molecular & Cellular Biochemistry 7:725, 1987.

Denison, S.H., Sands, A. and Tindall, D.J. Endocrinology 124:1091, 1989.

Dodd, J.G., Sheppard, P.C. and Matusik, R.J. Journal of Biological Chemistry 258:10731, 1983.

Dodd, J.G., Kreis, C., Sheppard, P.C., Hamel, A. and Matusik, R.J. Molecular & Cellular Endocrinology 47:191, 1986.

Dodd, J.G., Morris, G., Miller, T.L., et al. Oncogenes and the prostate. In: The prostate as an endocrine gland, edited by Farnsworth, W.E. and Ablin, R.J. Florida: CRC press, 1990, pp. 49-66.

Dodd, J.G., Paraskeva, M. and McNicol, P.J. J. Urol. 149:400, 1993.

Dubois, N., Bennoun, M., Allemand, I., et al. Journal of Hepatology 13:227, 1991.

Dyer, K.R. and Messing, A. American Journal of Pathology 135:401, 1989.

Efrat, S., Linde, S., Kofod, H., et al. Proceedings of the National Academy of Sciences of the United States of America 85:9037, 1988.

Eva, A., Graziani, G., Zannini, M., Merin, L.M., Khillan, J.S. and Overbeek, P.A. New Biologist 3:158, 1991.

Evans, R.M. Science 240:889, 1988.

Felgner, P.L. Laboratory Investigation 68:1, 1993.

Fenjves, E.S. and et al. Proceedings of the National Academy of Sciences of the United States of America 86:8803, 1989.

Fleming, W.H., Hamel, A., MacDonald, R., et al. Cancer Research 46:1535, 1986.

Folkman, J., Watson, K., Ingber, D. and Hanahan, D. Nature 339:58, 1989.

French, F.S., Lubahn, D.B., Brown, T.R., et al. Recent Progress in Hormone Research 46:1, 1990.

Friedmann, T. Cancer 70:1810, 1992.

Galiana, E., Borde, I., Marin, P., et al. Journal of Neuroscience Research 26:269, 1990.

Greenberg, M.N., Dodd, J.G., Duckworth, M.L., Rosen J.M. and Matusik, R.J. The Endocrine Society Jun. 9-11:Abstract 1206, 1993. (Abstract).

Greenberg, M.N., Matusik, R.J. and Rose, J.M. NIDDKD Sep. 11-13:1192a. (Abstract).

Greenberg, M.N., Rose, J.M. and Matusik, R.J. Prouts Neck Oct. 15-18:1992b. (Abstract).

Greenberg, N.M., Dodd, J.G., Duckworth, M.L., Rose, J.M. and Matusik, R.J. SBUR May 15:1993. (Abstract).

Ham, J., Thomson, A., Needham, M., Webb, P. and Parker, M. Nucleic Acids Research 16:5263, 1988.

Hamaguchi, K. and Leiter, E.H. Diabetes 39:415, 1990.

Hammang, J.P., Baetge, E.E., Behringer, R.R., Brinster, R.L., Palmiter, R.D. and Messing, A. Neuron 4:775, 1990.

Hanahan, D. Oncogenes and Growth Control. Kahn P et al. eds. New York, Springer-Verlag, pp. 349-363, 1986.

Harris, S.E., Harris, M.A., Johnson, C.M., et al. Journal of Biological Chemistry 265:9896, 1990.

He, W.W., Kumar, M.V. and Tindall, D.J. Nucleic Acids Research 19:2373, 1991.

Heyns, W., Peeters, B., Mous, J., Rombauts, W. and DeMoor, P. European Journal of Biochemistry 89:181, 1978.

Ho, K.C., Snoek, R., Quarmby, V., et al. Biochemistry 28:6367, 1989.

Ho, K.C., Quarmby, V.E., French, F.S. and Wilson, E.M. Journal of Biological Chemistry 267:12660, 1992.

Hockenbery, D. Proc Annu Meet Am Assoc Cancer Res; 33:A585-6, 1992.

Hurst, H. and Parker, M.G. Embo Journal 2:769, 1983.

Hyde, S.C., Gill, D.R., Higgins, C.F., et al. Nature 362:250, 1993.

Ichikawa, T., Ichikawa, Y., Dong, J., et al. Cancer Research 52:3486, 1992.

Imperato-McGinley, J., Ip, N.Y., Gautier, T., et al. American Journal of Medical Genetics 36:104, 1990.

Isaacs, W.B. and Carter, B.S. Cancer Surveys 11:15, 1991a.

Isaacs, W.B., Carter, B.S. and Ewing, C.M. Cancer Research 51:4716, 1991b.

Iwamoto, T., Takahashi, M., Ito, M., et al. Embo Journal 10:3167, 1991.

Iwamoto, T. Takahashi, M., Ohbayashi, M. and Nakashima, I. Experimental Cell Research 200:410, 1992.

Kazemi-Esfarjani, P., Beitel, L., Trifiro, M., et al. Molecular Endocrinology 7:37, 1993.

Klein-Hitpass, L., Schorpp, M., Wagner, U. and Ryffel, G.U. Cell 46:1053, 1986.

Knight, K.L., Spieker-Polet, H., Kazdin, D.S. and Oi, V.T. Proceedings of the National Academy of Sciences of the United States of America 85:3130, 1988.

Kuiper, G.G., de Ruiter, P.E., Trapman, J., Boersma, W.J., Grootegoed, J.A. and Brinkmann, A.O. Biochemical Journal 291:95, 1993.

La Spada, A.R., Wilson, E.M., Lubahn, D.B., Harding, A.E. and Fischbeck, K.H. Nature 352:77, 1991.

Langdon, W.Y., Harris, A.W. and Cory, S. Oncogene Research 4:253, 1989.

Larue, L., Dougherty, N., Bradl, M. and Mintz, B. Oncogene 8:523, 1993.

Leder, A., Patengale, P.K., Kuo, A., Stewart, T.A. and Leder, P. Cell 45:485, 1986.

Leder, P. Animal Model for Benign Prostatic Disease: Patent WO 90/09443, World Intellectual Property Organization, 1990. (UnPub).

Li, S., Klein, E.S., Russo, A.F., Simmons, D.M. and Rosefeld, M.G. Proceedings of the National Academy of Sciences of the United States of America 86:9778, 1989.

Lin, T.P., Guzman, R.C., Osborn, R.C., Thordarson, G. and Nandi, S. Cancer Research 52:4413, 1992.

Lubahn, D.B., Brown, T.R., Simental, J.A., et al. Proceedings of the National Academy of Sciences of the United States of America 86:9534, 1989.

Lucchini, F., Sacco, M.G., Hu, N. et al. Cancer Leggers 64:203, 1992.

Martinez de la Escalera, G., Choi, A.L. and Weiner, R.I. Proceedings of the National Academy of Sciences of the United States of America 89:1852, 1992.

Matsui, Y., Halter, S.A., Holt, J.T., Hogan, B.L. and Coffey, R.J. Cell 61:1147, 1990.

Matusik, R.J., Kreis, C. McNicol, P., et al. Biochemistry & Cell Biology 64:601, 1986.

Matusik, R.J., Fleming, W.H., Hamel, A., et al. Progress in Clinical & Biological Research 239:91, 1987.

Matzuk, M.M., Finegold, M.J., Su, J.G.J., Hsueh, A.J.W. and Bradley, A. Nature 360:313, 1992.

Mayo, K.E., Hammer, R.E., Swanson, L.W., Brinster, R.L., Rosenfeld, M.G. and Evans, R.M. Molecular Endocrinology 2:606, 1988.

McKnight, R.A. Shamay, A., Sankaran, L., Wall, R.J. and Hennighausen, L. Proceedings of the National Academy of Sciences of the United States of America 89:6943, 1992.

McNicol, P.J. and Dodd, J.G. Journal of Clinical Microbiology 28:409, 1990a.

McNicol, P.J. and Dodd, J.G. Canadian Journal of Microbiology 36:359, 1990b.

McNicol, P.D. and Dodd, J.G. J. Urol. 145:850, 1991.

Mellon, P.L., Wetsel, W.C., Windle, J.J., et al. Ciba Foundation Symposium 168:104, 1992.

Montgomery, B.T., Young, C.Y., Bilhartz, D.L., et al. Prostate 21:63, 1992.

Morris, G.L. and Dodd, J.G. J. Urol. 143:1272, 1990.

Morton, R.A., Isaacs, J.T. and Isaacs, W.B. Prostate 17:327, 1990.

Mougneau, E., Meneguzzi, G. and Cuzin, F. Genes and Signal Transduction in Multistage Carcinogenesis. Colburn NH, ed., New York, Marcel Dekker, pp. 221–229, 1989.

Mukhopadhyay, T. and et al. Cancer Research 51:1744, 1991.

Muller, W.J., Sinn, E., Pattengale, P.K., Wallace, R. and Leder, P. Cell 54:105, 1988.

Muller, W.J., Lee, F.S., Dickson, C., Peters, G., Pattengale, P. and Leder, P. Embo Journal 9:907, 1990.

Muller, W.J. Cancer & Metastasis Reviews 1–:217, 1991.

Mulligan, R.C. Science 260:926, 1993.

Murphy, B.C., Pienta, K.J. and Coffey, D.S. Prostate 20:29, 1992.

Nachtigal, N.W., Nickel, B.E., Klassen, M.E., Zhang, W., Eberhardt, N.L. and Cattini, P.A. Nucleic Acids Research 17:4327, 1989.

Newmark, J.R., Hardy, D.O., Tonb, D.C., et al. Proceedings of the National Academy of Sciences of the United States of America 89:6319, 1992.

Parker, M.G., White, R. and Williams, J.G. Journal of Biological Chemistry 255:6996, 1980.

Parker, M.G. and Needham, M. In: Regulation of androgen action, edited by Bruchovsky, N., Chapdelaine, A. and Neumann, F. Berlin: Congressdruck R. Bruckner, 1985, pp. 175–178.

Parker, M.G., Webb, P., Mills, J.S., Needham, M. and White, R. Journal of Steroid Biochemistry 30:47, 1988.

Pawson, T. Dev Oncol; 51:155–72 1987.

Peehl, D.M. Cancer 71:1159, 1993.

Perry, S.T., Viskochil, D.H., Ho, K.C., et al. In: Regulation of androgen action, edited by Bruchovsky, N., Chapdelaine, A. and Neumann, F. Berlin: Congressdruck R. Bruckner, 1985 pp. 167–173.

Pienta, K.J., Isaacs, W.B., Vindivich, D. and Coffey, D.S. J. Urol. 145:199, 1991.

Power, R.F., Mani, S.K., Codina, J., Conneely, O.M. and O'Malley, B.W. Science 254:1636, 1991.

Quigley, C.A., Evans, B.A., Simental, J.A., et al. Molecular Endocrinology 6:1103, 1992.

Rennie, P.S., Bowden, J.F., Freeman, S.N., et al. Molecular Endocrinology 3:703, 1989.

Rennie, P.S., Bruchovsky, N., Leco, K.J., et al. Molecular Endocrinology 7:23, 1993.

Reynolds, R.K. Hoekzema, G.S., Vogel, J., Hinrichs, S.H. and Jay, G. Proceedings of the National Academy of Sciences of the United States of America 85:3135, 1988.

Riegman, P.H., Vlietstra, R.J., van der Korput, J.A., Brinkmann, A.O. and Trapman, J. Molecular Endocrinology 5:1921, 1991.

Rindi, G., Efrat, S., Ghatei, M.A., Bloom, S.R., Solcia, E. and Polak, J.M. Virchows Archiv—A. Pathological Anatomy & Histopathology 419:115, 1991.

Ris–Stalpers, C., Trifiro, M.A., Kuiper, G.G., et al. Molecular Endocrinology 5:1562, 1991.

Roche, P.J., Hoarse, S.A. and Parker, M.G. Molecular Endocrinology 6:2229, 1992.

Rushmere, N.K., Claessens, F., Peeters, B., Rombauts, W. and Davies, P. Biochemical Society Transactions 18:560, 1990.

Russo, A.F., Crenshaw, E.B., Lira, S.A., Simmons, D.M., Swanson, L.W. and Rosefeld, M.G. Neuron 1:311, 1988.

Sandgren, E. P., Quaife, C.J., Pikert, C.A., Palmiter, R.D. and Brinster, R.L. Oncogene 4:715, 1989.

Sandgren, E.P., Luetteke, N.C., Qiu, T.H., Palmiter, R.D., Brinster, R.L. and Lee, D.C. Molecular & Cellular Biology 13:320, 1993.

Schechter, J., Windle, J.J., Sauber, C. and Mellon, P.L. Neuroendocrinology 56:300, 1992.

Scheidereit, C., Westphal, H.M., Carlson, C., Bosshard, H. and Beato, M. DNA 5:383, 1986.

Shemshedini, L., Ji, J.W., Brou, C., Chambon, P. and Gronemeyer, H. Journal of Biological Chemistry 267.:1834, 1992.

Short, M.P. and et al. Journal of Neuroscience Research 27:427, 1990.

Shrale, U., Klock, G. and Schutz, G. Proceedings of the National Academy of Sciences of the United States of America 84:7871, 1987.

Simental, J.A., Star, M. and Wilson, E.M. Journal of Steroid Biochemistry & Molecular Biology 43:37, 1992.

Sinkovics, J.G. Critical Reviews in Oncology–Hematology 11:87, 1991.

Skalnik, D.G., Dorfman, D.M., Williams, D.A. and Orkin, S.H. Molecular & Cellular Biology 11:4518, 1991.

Smith, D.F. and Toft, D.O. Molecular Endocrinology 7:4, 1993.

Spence, A.M., Sheppard, P.C., Davie, J.R., et al. Proceedings of the National Academy of Sciences of the United States of America 86:7843, 1989.

Stamp, G., Fantl, V., Poulsom, R., et al. Cell Growth & Differentiation 3:929, 1992.

Stefaneau, L. Rindi, G., Horvath, E., Murphy, D., Polak, J.M. and Kovacs, K. Endocrinology 130:1789, 1992.

Strange, R. and Cardiff, R.D. Dev Oncol; 58:1–14, 1990.

Sweetland R., Sheppard, P.C., Dodd, J.G. and Matusik, R.J. Molecular & Cellular Biochemistry 84:3, 1988.

Tal, M., Thorens, b., Surana, M., et al. Molecular & Cellular Biology 12:422, 1992.

Tan, J., Marschke, K.B., Ho, K.C., Perry, S.T., Wilson, E.M. and French, F.S. Journal of Biological Chemistry 267:7958, 1992.

Thompson, T.C., Truong, L.D., Timme, T.L., et al. Cancer 71:1165, 1993.

Tolstoshev, P. and Anderson, W.F. Gene transfer techniques in human gene therapy. In: Genome Research in Molecular Medicine and Virology, Academic Press, Inc., 1993.

Tutrone, R.F., Jr., Ball, R.A., Ornitz, D.M., Leder, P. and Richie, J.P. J. Urol 149:633, 1993.

Umesono, K., Giguere, V., Glass, C.K., Rosefeld, M.G. and Evans, R.M. Nature 336:262, 1988.

Vaux, D.L., Cory, S. and Adams, J.M. Nature 335:440, 1988.

Veldscholte, J., Ris–Stalpers, C., Kuiper, G.G., et al. Biochemical & Biophysical Research Communications 173:534, 1990.

Veldscholte, J., Berrevoets, C.A., Brinkmann, A.O., Grootegoed, J.A. and Mulder, E. Biochemistry 31:2393, 1992a.

Veldscholte, J., Berrevoets, C.A., Ris–Stalpers, C., et al. Journal of Steroid Biochemistry & Molecular Biology 41:665, 1992b.

Von Deimling, A., Aguzzi, A., Kleihues, P., Land, H. and Wiestler, O.D. Verhandlungen Der Deutschen Gesellschaft Fur Pathologie 74:432, 1990.

Von der Ahe, D., Pearson, D., Nakagawa, J., Rajput, B. and Nagamine, Y. Nucleic Acids Research 16:7527, 1993.

Windle, J.J., Weiner, R.I. and Mellon, P.L. Molecular Endocrinology 4:597, 1990.

Wooster, R., Mangion, J., Eeles, R., et al. Nature Genetics 2:132, 1992.

Yamamura, K. Gan To Kagaku Ryoho 16:733, 1989.

Yarbrough, W.G., Quarmby, V.E., Simental, J.A., et al. Journal of Biological Chemistry 265:8893, 1990.

Young C.Y., Andrews, P.E., Montgomery, B.T. and Tindall, D.J. Biochemistry 31:818, 1992.

Zhu N., Liggitt D., Liw Y., Debs R. "Systemic Gene Expression after Intravenous DNA Delivery into Adult Mice", Science 261:209–211, 1993.

Cartier, N., Lacave, R., Vallet, V., Hagege, J., Hellio, R., Robine, S., Pringault, e., Cluzeaud, F., Briand, P., Kahn, A., and et al. (1993). Establishment of renal proximal tubule cell lines by targeted oncogenesis in transgenic mice using the L–pyruvate Kinase–SV40 (T) antigen hybrid gene. J. Cell Sci. 104, 695–704.

Chen, J., Tobin, G.J., Pipas, J.M., and Van Dyke, T. (1992). T–antigen mutant activities in vivo: roles of p53 and pRB binding in tumorigenesis of the choroid plexus. Oncogene 7, 1167–1175.

D'Ambra, R., Surana, M., Efrat, S., Starr, R.G., and Fleischer, N. (1990). Regulation of insulin secretion from beta-cell lines derived from transgenic mice insulinomas resembles that of normal beta-cells. Endocrinology 126, 2815–2822.

De Vos, P., Claessens, F., Peeters, B., Rombauts, W., Heyns, W., and Verhoeven, G. (1993). Interaction of androgen and glucocorticoid receptor DNA–binding domains with their response elements. Mol. Cell Endocrinol. 90, R11–R16.

Greenberg, N.M., DeMayo, F.J., Sheppard, P.C., Barrios, R., Lebovitz, M., Fingold, M., Angelopoulou, R., Dodd, J.G., Duckworth, M.L., Rosen, J.M., and Matusik, R.J. (1994). The rate probasin gene promoter directs hormonally and developmentally regulated expression of a heterologous gene specifically to the prostate in transgenic mice. Molecular Endocrinology 8, 230–239.

Griep, A.E. and Westphal, H. (1990). Differentiation versus proliferation of transgenic mouse lens cells expressing polyoma large T antigen: evidence for regulation by an endogenous growth factor. New Biol. 2, 727–738.

Guyette, W.A., Matusik, R.J., and Rosen, J.M. (1979). Prolactin–mediated transcriptional and post–transcriptional control of casein gene expression. Cell 17, 1013–1023.

Kasper, S., Yan, Y., Lin, L., Sheppard, P.C., Kurtzman, G., and Matusik, R.J. (1994). Gene therapy for prostate cancer: The adeno–associated virus coupled to probasin DNA will direct transgenes in prostate specific expression. SBUR May 13–14, Abstract, San Francisco, CA.

Katz, E.B., Steinhelper, M.E., Delcarpio, J.B., Daud, A.I., Claycomb, W.C., and Field, L.J. (1992). Cardiomyocyte proliferation in mice expressing alph–cardiac myosin heavy chain–SV40 T–antigen transgenes. Am. J. Physiol. 262, H1867–H1876.

Kitagawa, T., Hino, O., Lee, G.H., Li, H., Liu, J., Nomura, K., Ohtake, K., Furuta, Y., and Aizawa, S. (1991). Multisteph hepatocarcinogenesis in transgenic mice harboring SV40 T–antigen gene. Princess. Takamatsu. Symp. 22, 349–360.

Lacave, R., Bens, M., Cartier, N., Vallet, V., Robine, S., Pringault, E., Kahn, A., and Vandewalle, A. (1993). Functional properties of proximal tubule cell lines derived from transgenic mice harboring L–pyruvate kinase–SV40 (T) antigen hybrid gene. J. Cell Sci. 104, 705–712.

Levine, A.J. (1989). The p53 tumor suppressor gene and gene product. Princess. Takamatsu. Symp. 20, 221–230.

Maroulakou, I., Garrett, L., Anver, M., Papas, T., and Green, J. (1994). Prostate and breast adenocarcinoma development in transgenic mice. Breast and Prostate Cancer II Abstract 306, Mar. 14–20–Lake Tahoe, CA. (Abstract).

Matuo, Y., Adams, P.S., Nishi, N., Yasumitsu, H., Crabb, J.W., matusik, R.J., and McKeehan, W.L. (1989). The androgen–dependent rat prostate protein probasin, is a heparin–binding protein that co–purifies with heparin–binding growth factor–1. In Vitro Cellular & Developmental Biology 25, 581–584.

Nevalainen, M.T., Valve, E.M., Makela, S.I., Blauer, M., Tuohimaa, P.J., and Harkonen, P.L. (1991). Estrogen and prolactin regulation of rat dorsal and lateral prostate in organ culture. Endocrinology 129, 612–622.

Page, M.J. and Parker, M.G. (1982). Effect of androgens on the transcription of rat prostatic binding protein genes. Molecular and Cellular Endocrinology 27, 343–355.

Paquis Flucklinger, V., Michiels, J.F., Vidal, F., Alquier, C., Pointis, G., Bourdon, V., Cuzin, F., and Rassoulzadegan, M. (1993). Expression in transgenic mice of the large T antigen of polyomavirus induces Sertoli cell tumours and allows the establishment of differentiated cell lines. Oncogene 7, 2087–2094.

Rassoulzadegan, M., Paquis Flucklinger, V., Bertino, B., Sage, J., Jasin, M., Miyagawa, K., van Heyningen V., Besmer, P., and Cuzin F. (1993). Transmeiotic differentiation of male germ cells in culture. Cell 75, 997–1006.

Rindi, G., Grant, S.G., Yiangou, Y., Ghatei, M.A., Bloom, S.R., Bautch, V.L., Solcia, E., and Polak, J.M. (1990). Development of Neuroendocrine tumors in the gastrointestinal tract of transgenic mice. Heterogeneity of hormone expression. Am. J. Pathol. 136, 1349–1363.

Rouleau, M., Leger, J., and Tenniswood, M. (1990). Ductal heterogeneity of cytokeratins, gene expression, and cell death in the rat ventral prostate. Mol. Endocrinol. 4, 2003–2013.

Smith, M.S., Lechago, J., Wines, D.R., MacDonald, R.J., and Hammer, R.E. (1992). Tissue-specific expression of kallikrein family transgenes in mice and rats. DNA Cell Biol. 11, 345–358.

Sugiyama, N. Tabuchi, Y., Horiuchi, T., Obinata, M., and Furusawa, M. (1993). Establishment of gastric surface mucous cell lines from transgenic mice harboring temperature-sensitive simian virus 40 large T-antigen gene. Exp. Cell Res. 209, 382–387.

Symonds, H., Chen, J.D., and Van Dyke, T. (1991). Complex formation between the lymphotropic papovavirus large tumor antigen and the tumor suppressor protein p53. J. Virol. 65, 5417–5424. 262, H1867–H1876.

Tanaka, Y., Mamalaki, C., Stockinger, B., and Kloussis, D. (1993). In vitro negative selection of alpha beta T cell receptor transgenic thymocytes by conditionally immortalized thymic cortical epithelial cell lines and dendritic cells. Eur. J. Immunol. 23, 2614–2621.

Weber Benarous, A., Decaux, J.F., Bennoun, M., Allemand, I., Briand, P., and Kahn, A. (1993). Retroviral infection of primary hepatocytes from normal mice and mice transgenic for SV40 large T antigen. Exp. Cell Res. 205, 91–100.

Yanai, N., Satoh, T., Kyo, S., Abe, K., Suzuki, M., and Obinata, M. (1991a). A tubule cell line established from transgenic mice harboring temperature-sensitive simian virus 40 large T-antigen gene. Jpn. J. Cancer Res. 82, 1344–1348.

Yanai, N., Suzuki, M., and Obinata, M. (1991b). Hepatocyte cell lines established from transgenic mice harboring temperature-sensitive simian virus 40 large T-antigen gene. Exp. Cell Res. 197, 50–56.

AAGCTTCCACAAGTGCATTTAGCCTCTCTCCAGTATTGCTGATGAATCCACAGTTCAGGTTC

AATGGGCGTTCAAAAATGACCAGACTTTATATTCTTACACCAACATCTAT

CTGATTGGAGGAATGGATAATAGTCATCATGTTTAAACATCTACCATTCCAGTTAAGAAA

ATATGATAGCATCTTGTTCTTAGTCTTTTTCTTAATAGGGACATAAAGCCCACAAATAAA

AATATGCCTGAAGAATGGGACAGGCATTGTCCATGCCTAGTAAAGTACTCCAA

FIG. 1B

```
                        -101  -95                    -82      -75
                          *    *                      *        *
GAACCTATTTGTATACTAGATGACACAATGTCAATGTCTGTGTACAACTGCCAACTGGGA

-27
                                                    *
TGCAAGACACTGCCCATGCCAATCATCCTGAAAAGCAGCTATAAAAAGCAGGAAGCTACT
        *
       -48

+1                                    +28
  v*                                     *
CTGCACCTTGTCAGTGAGGTCCAGATACCTACAGAGCTCACACACG ATG AGG GTC
                                                Met Arg Val

ATC CTC CTC CTG CTC ACA CTG CTC GAT GTG CTA GGT GTC TCC AGT
Ile Leu Leu Leu Leu Thr Leu Leu Asp Val Leu Gly Val Ser Ser

ATG ATG ACA GAC AAG AAT CTC AAA AAG AAG GTAGCAGAC
Met Met Thr Asp Lys Asn Leu Lys Lys Lys
```

ANDROGEN REGULATION WITH DNA SEQUENCES OF RAT PROBASIN GENE

CONTINUING DATA

This application is a national stage application of PCT/CA93/00319, filed Aug. 9, 1993 and claims priority under 35 USC 119 to GB 9216851.7, filed Aug. 7, 1992.

FIELD OF THE INVENTION

The present invention is concerned with a novel DNA molecule and fragments thereof, which permits production of an (1) assay for androgenic or anti-androgenic materials, (2) transgenic non-human eukaryotic animals models for prostatic disease, (3) cell culture models for prostatic disease, and (4) treatment of human benign prostatic hyperplasia and human prostate cancer by gene therapy. This invention permits assays on agonist and antagonist of the androgen receptor or pathways that result in androgen action, testing materials for carcinogenicity on the prostate, testing drugs and gene therapy, or protection potential of materials on prostatic cells against prostatic disease.

BACKGROUND OF THE INVENTION

Androgen Activity

A clinical need to assay the function of the androgen receptor (AR) occurs when defects appear in the pathway of androgen action. For example, mutations in the AR affect the bioactivity of the receptor in Androgen Insensitivity Syndrome, AIS, (Kazemi-Esfarjani et al., 1993; Brinkmann et al., 1991; Brinkmann et al., 1992a; Brinkmann et al., 1992b; De Bellis et al., 1992; French et al., 1990; Imperato-McGinley et al., 1990; Lubahn et al., 1989; Quigley et al., 1992; Ris-Stalpers et al., 1990; Ris-Stalpers et al., 1991; Simental et al., 1992) or testicular feminized animals (Yarbrough et al., 1990; He et al., 1991), Kennedy Syndrome (La Spada et al., 1991), prostate cancer (Newmark et al., 1992; Brinkmann et al., 1991; Veldscholte et al., 1992b; Veldscholte et al., 1992a; Veldscholte et al., 1990) and breast cancer (Wooster et al., 1992). Besides mutations directly in the receptor, defects can occur in the non-androgenic mechanism for steroid receptor activation as has been reported for steroid receptors (Power et al., 1991; Shemshedini et al., 1992; Kuiper et al., 1993). An assay that would measure the extent of these defects would also provide a tool to test new materials that may activate the defective receptor and form the basis of a therapy.

Androgen receptors are members of a nuclear receptor superfamily which are believed to function primarily as transcription factors that regulate gene activity through binding specific DNA sequences to hormone responsive elements (HRE) and associated factors (Allan et al., 1991; Smith et al., 1993; Evans, 1988; Beato, 1989). In general, these HREs can be grouped into two categories of inverted repeat consensus sequences: the TGACC motif that mediates estrogen, retinoic acid, and thyroid hormone responses (Klein-Hitpass et al., 1986; Umesono et al., 1988); and the TGTTCT sequence that confers regulation by glucocorticoids, progestins and androgens (Scheidereit et al., 1986; Shrahle et al., 1987; Ham et al., 1988). The inclusion of the androgen receptor responsive element (ARE) in this latter group is based largely on observed binding of androgen receptors to the glucocorticoid responsive element (GRE) of mouse mammary tumor virus (MMTV) DNA (Ham et al., 1988; Roche et al., 1992; Darbre et al., 1986; Cato et al., 1987) and the tyrosine aminotransferase (TAT) gene (Denison et al., 1989).

Androgen regulation of the C3(1) gene which encodes a polypeptide component of prostatic steroid-binding protein has been investigated (Heyns et al., 1978; Hurst et al., 1983; Parker et al., 1988; Parker et al., 1980). Although sequences within both the promoter region and first intron of the C3(1) gene have high affinity binding for androgen receptors (Perry et al., 1985; Claessens et al., 1993; De Vos et al., 1991; Rushmere et al., 1990), attempts to use these sequences to confer androgen regulation on a homologous or heterologous promoter-reporter system have met with limited success (Parker et al., 1985; Parker et al., 1988); with only a weak androgen induction seen with these genomic fragments (Claessens et al., 1993; Tan et al., 1992; De Vos et al., 1991; Rushmere et al., 1990; Claessens et al., 1990b; Claessens et al., 1990a; Claessens et al., 1989b; Claessens et al., 1989a). Recently, DNase I footprinting experiments have shown that the DNA-binding domain of the androgen receptor binds to a glucocorticoid responsive element (GRE) present in this intronic fragment (De Vos et al., 1991; Claessens et al., 1993). The occurrence of a complete GRE in this gene is consistent with the observed effects of glucocorticoids on the expression of the C1 component of prostatic binding protein (Rennie et al., 1989). The human prostate specific antigen (PSA) gene is androgen regulated in human prostate tumors and in cell culture (Riegman et al., 1991; Montgomery et al., 1992; Young et al., 1992; Murphy et al., 1992; Armbruster, 1993). Construction of the PSA DNA promoter reveal a GRE-like sequence that responds to androgens (Riegman et al., 1991). The Slp gene demonstrates specific androgen regulation via GRE-like sequences (Adler et al., 1992; Adler et al., 1991). Other androgen regulated genes from the prostate have been cloned, such as the SVS II (Dodd et al., 1983; Dodd et al., 1986; Harris et al., 1990), 20 kDa protein (Ho et al., 1989), and DP1 (Ho et al., 1992), but the androgen regulatory sequences have not been identified.

Transgenic animals

The introduction of a gene into the germline at the one cell or early embryonic stage produces a transgenic animal which will contain and pass on the gene to its offspring. Tissue specific expression of a gene can be restricted by tissue specific elements with the DNA. Success with prostate specific expression of transgenes has been limited and often not restricted to the prostate. For example, the complete rat C3(1) gene including 4.3 kb of 5'-flanking sequence and 2.2 kb of 3'-flanking sequence will give prostate specific expression in transgenic mice (Allison et al., 1989), but using only the 6 kb of 5'-flanking C3(1) resulted in transgenic lines that targeted to the prostate, seminal vesicles, and testis (Buttyan et al., 1993). MMTV coupled to int-2 produced a transgenic mouse line that developed prostatic epithelial cell hyperplasia that was androgen regulated but the males are sterile (Muller et al., 1990; Leder, 1990; Tutrone et al., 1993). Various males in different lines, in addition to expressing the transgene in the prostate, also expressed the int-2 gene in the seminal vesicles, vas deferens, salivary gland while the females expressed the gene in the mammary gland and developed mammary hyperplasia (Leder, 1990). However, targeting with MMTV can lead to expression in the testis resulting in sterility (Lucchini et al., 1992). Using the gp91-phox gene promoter (a gene not normally expressed in the prostate) linked to the early region of SV-40 virus, lesions in the prostate defined as neuroblastomas were created (Skalnik et al., 1991).

Any gene targeted to the prostate in transgenic animals may alter prostatic growth and function. Oncogenes and tumor suppressor genes (Fleming et al., 1986; Matusik et al., 1987; Dodd et al., 1990; Hockenbery, 1992; Buttyan et al., 1993; Carter et al., 1990a; Carter et al., 1990b; Tutrone et al., 1993; Bookstein et al., 1993; Thompson et al., 1993; Peehl, 1993; Dodd et al., 1993; McNicol et al., 1991; McNicol et al., 1990a; McNicol et al., 1990b) as well as growth factors (Morris et al., 1990; Ichikawa et al., 1992; Isaacs et al., 1991a; Isaacs et al., 1991b; Carter et al.,1990a; Pienta et al., 1991; Morton et al., 1990) implicated in the development of prostatic hyperplasia or cancer are likely starting points. In addition, genes such as the large T antigen, which successfully induce cancer in endocrine glands when targeted in transgenic animals, are suitable candidates (Anonymous, 1991; Stefaneanu et al., 1992; Hanahan, 1986; Rindi et al., 1991; Hamaguchi et al., 1990).

Transgenic animals that express the transgene in a tissue or non-tissue specific can result in new models. For example, non-tissue specific expression can result in diseased states in a number of tissues while tissue specific expression of targeted genes can lead to disease states in targeted organs as follows: cancer models (Burck et al., 1988; Yamamura, 1989; Folkman et al., 1989; Reynolds et al., 1988; Anonymous, 1992; Bautch, 1989; Hanahan, 1986; Lucchini et al., 1992; Anonymous, 1988); mammary adenocarcinoma (Muller et al., 1988; Muller, 1991; Pawson, 1987; Callahan et al., 1989; Muller, 1991; Strange et al., 1990); hyperplasia and dysplasia (Mayo et al., 1988; Borrelli et al., 1992; Eva et al., 1991; Lin et al., 1992; Matsui et al., 1990); neuroblastomas (Dalemans et al., 1990); liver cancer (Butel et al., 1990; Dubois et al., 1991; Sandgren et al., 1993; Sandgren et al., 1989); gonadal tumors (Schechter et al., 1992; Matzuk et al., 1992); thymic mesenchymal tumors (Sinkovics, 1991); and leukaemia (Knight et al., 1988; Adams et al., 1985). Further, targeted genes may function to accelerate tumor formation by conferring susceptibility to transformation by factors or carcinogens (Langdon et al., 1989; Breuer et al., 1989; Mougneau et al., 1989). Promoters, such as metallothionein (MT), often lead to general expression in many organs (Dyer et al., 1989; Iwamoto et al., 1991) while the MMTV promoter limits expression to endocrine target tissues due to its HRE (Ham et al., 1988; Roche et al., 1992; Darbre et al., 1986; Cato et al., 1987). Even using a general promoter can lead to specific effects if the factor expressed targets a specific tissue, i.e. MT-growth hormone releasing factor (Mayo et al., 1988) or ectopic nerve growth factor (Borrelli et al., 1992) lead to pituitary hyperplasia in transgenic mice.

Gene therapy

The treatment of human disease or disease in non-human eukaryotic animals by gene therapy started with the goal to correct single-gene inherited defects. Advances have expanded that goal to include the treatment of acquired diseases, such as cancers (Davies, 1993; Anderson, 1992; Mulligan, 1993; Culotta, 1993; Felgner, 1993; Tolstoshev et al., 1993). Approved clinical trials are presenting encouraging results. The practical problem has been the development of efficient and specific approaches that will transfer and express a gene within the correct cell type. The approaches can be classed as viral and nonviral methods to transfer genes. Some of the therapeutic approaches transfer the gene(s) to patient cells which have been cultured and then returned to the same individual (Fenjves et al., 1989). Others attempt direct transfer of the gene to the human tissue. For example, a DNA complex with liposomes can be delivered to the airway and correct the cystic fibrosis defect in transgenic mice (Hyde et al., 1993). Direct gene transfer by DNA: cationic liposomes into adult mice demonstrates efficient transfer and expression occurs in most organs (Zhu et al., 1993). If the gene is stably integrated, then the defect may be corrected while, if the gene was transiently expressed, then a relief in the disease would likely be transient. However, in cases, such as cancer, where the goal is to kill the cancerous cell, transient expression would be sufficient if the expressed gene is toxic (Short et al., 1990; Culver et al., 1992). Approaches may include expressing tumor suppressor genes (Friedmann, 1992) or genes to inhibit expressed oncogenes (Mukhopadhyay et al., 1991).

SUMMARY OF THE INVENTION

In one aspect, the present invention provides an isolated DNA molecule comprising a 5'-flanking region of the rat probasin gene and containing at least one androgen responsive element, preferably two such elements. The DNA molecule preferably has the sequence shown in FIG. 1 (SEQ ID NO: 1) or one which hybridizes thereto under stringent conditions (SEQ ID NO: 2 shows the derived amino acids for the amino acid coding portion of the DNA molecule).

In another aspect of the invention, there is provided an isolated DNA molecule comprising an androgen responsive element of the rat probasin gene or a mutation thereof retaining androgen activity, preferably, the DNA sequence comprises nucleotides −241 to −223 and/or nucleotides −140 to −117, as seen in FIG. 1, or a mutation thereof retaining androgen activity. In one embodiment, nucleotides −130 to −127 are replaced by nucleotides TACT (SEQ ID NO: 3) or GTCT (SEQ ID NO: 4).

The present invention includes not only the isolated and purified PB nucleotide sequences but also includes (1) an assay for androgenic or anti-androgenic materials, (2) transgenic non-human eukaryotic animals models for prostatic disease, (3) cell culture models for prostatic disease, (4) treatment of human benign prostatic hyperplasia and human prostate cancer employing such DNA sequences. The present invention permits assays on agonist and antagonist of the androgen receptor or pathways that result in androgen action, testing materials for carcinogenicity on the prostate, testing drugs and gene therapy, and protection potential of materials on prostatic cells against prostatic disease.

First, the Figures and Tables will be described. Unless otherwise stated, all bioassays of PB constructs are performed in PC-3 cells with the cotransfection of the appropriate steroid receptor expression vector (Rennie et al., 1993; Kazemi-Esfarjani et al., 1993).

BRIEF DESCRIPTION OF DRAWINGS

FIG. 1 shows the PB rat genomic sequence from −426 to +28 bp (SEQ ID NO: 1). The start of transcription is shown as v with the number starting immediately after as +1. All negative numbering is relative to the start site of transcription. Sequences beyond +28 define additional leader sequences and amino acid sequence of the first exon for PB. By sequence homology, the GRE-like sequence (ARE-1), CAAT box (SEQ ID NO: 5), and TATAA box (SEQ ID NO: 6) are underlined.

BRIEF DESCRIPTION OF TABLES

Figure 2A:
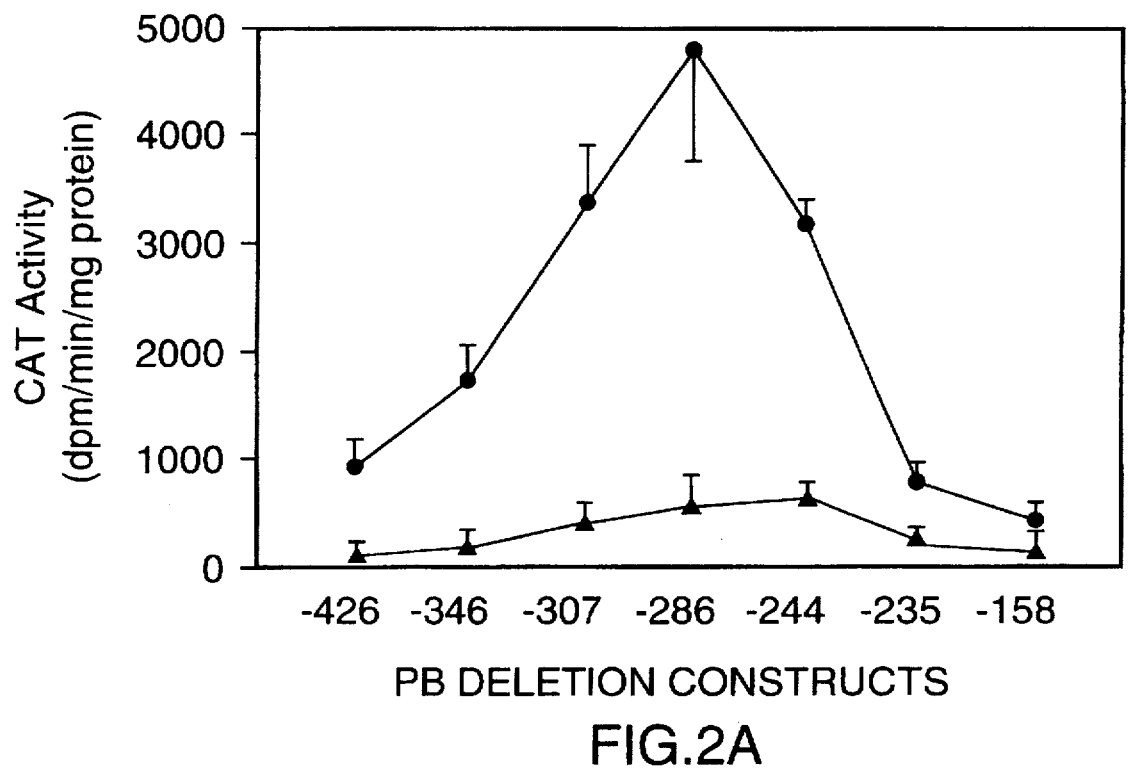
FIG. 2 shows the deletion mapping of PB 5'-flanking sequences (−426, −346, −307, −286, −244, −235, −157 bp) in PB-CAT, co-transfected in PC-3 cells with rAR or rGR expression vectors plus DHT (solid circles) or DEX (solid triangles), respectively. Activity of CAT with the rAR (open circles) or rGR (open triangles) expression vector without hormone addition served as the baseline (lower panel).

Table I shows the hormonal induction of PB-CAT in HeLa and PC-3 cells with DHT, DEX, and progestin.

Table II shows that the specific/tight AR binding is dependent upon both ARE sites as well as adjacent DNA sequences.

Table III shows that the bioactivity and specificity for AR is dependent upon both AREs as well as adjacent DNA sequences.

Table IV shows the bioactivity of −286 PB-ARE2*CAT compared for wild type −286 PB-CAT for wild type AR and when valine-865 is substituted by methionine or leucine in AIS.

Table V shows the bioassay effect on androgen induction when repeats −244 to −96 adjacent to TK-Luc.

Table VI shows the sensitivity increase to very low levels of androgen compared to the glucocorticoid DEX when the repeat n=3.

Table VII shows the sensitivity increase of repeat n=3 to detect differences in the wild type human AR from AIS samples.

Table VIII shows the high PB-CAT activity in the prostatic lobes of transgenic line #4248.

Table IX shows PB-CAT transgenic line #4248 expression in the mouse compared the endogenous rat PB gene. Expression in lateral lobe is taken as 100% and all other expression is compared relative to this value.

Table X shows the PB-CAT transgenic line #4248 expression after castration and androgen or glucocorticoid replacement.

DESCRIPTION OF THE PREFERRED EMBODIMENTS

1) Assay for Androgenic or Anti-Androgenic Materials.

The inventor has isolated and sequenced (FIG. 1) the 5'-flanking DNA of the rat probasin (PB) gene which is expressed specifically in the prostatic lobes and detectable in the seminal vesicles (Matusik et al., 1986). The probasin gene codes for a secreted and nuclear protein (Spence et al., 1989), which is androgen regulated in vivo and in vitro (Dodd et al., 1983; Rennie et al., 1993).

Isolation of Genomic Probasin Clone

To isolate the 5'-flanking DNA of the PB gene, pM-40 (Dodd et al., 1983), a cDNA clone which contains the complete coding region for PB (Spence et al., 1989), was used to screen a rat genomic library. Four positive clones were initially isolated and found to be identical after restriction and hybridization analysis. After subcloning into pUC119, the genomic clones were bidirectionally sequenced. The sequence of the 5'-flanking DNA of PB between −426 to +28 base pair (bp) is shown in FIG. 1. The 5' boundary of exon 1 was defined by both primer extension and S1 nuclease mapping (Spence et al., 1989). A major transcription start site (position 0) is followed four bp downstream by a minor start site. The canonical CAAT and TATAA boxes are underlined in FIG. 1 and located at −48 and −27 respectively. Four similar CAAT boxes are found at −101, −95, −82, and −75.

DNase I Footprinting Analysis

The DNase I footprinting was performed essentially as described (Von der Ahe et al., 1993; Rennie et al., 1993). Proteins (10 ng to 18 µg) were incubated with 20,000 cpm of the labelled DNA in 100 µl of DNA binding buffer for 30 min at 20° C. After adjusting the samples to 4 mM MgCl$_2$ and 2.5 CaCl$_2$ mM, 5 ng of DNase I was added and allowed to digest the DNA for 2 minutes at 20° C. The reaction was stopped by adding 100 µl of stop buffer (0.25% SDS, 0.3M EGTA, and 500 µg/ml of proteinase K) and incubated for 1 hour at 37° C. The samples were extracted with phenol-chloroform; precipitated with 0.2M sodium acetate, 85 µg/ml carrier tRNA, and 2 volumes of ethanol; redissolved in 3 µl of formamide dye solution. After heating at 70° C. for 10 minutes and rapid cooling on ice, the samples were loaded, together with an A+G Maxam-Gilbert sequencing reaction to obtain a purine ladder, on 7% polyacrylamide/urea gels (acrylamide:bis, 30:1) and run (Rennie et al., 1993). The gels were dried and set up for autoradiography.

The androgen response elements (ARE) are located at −241 to −223 (ARE-1) and −140 to −117 (ARE-2). The sequence of ARE-1 and ARE-2 in the 5'-flanking PB DNA were determined using DNase I footprinting assays with peptides containing the DNA-binding domain of the androgen receptor and later bioassay of the functional domains. The DNA- and steroid-binding domains of the rat androgen receptor (GST-AR1) and the DNA-binding domain and hinge region alone (GST-AR2) were expressed in E. coli as fusion proteins with glutathione-S-transferase and purified using glutathione affinity chromatography (Rennie et al., 1993). Both GST-AR1 and GST-AR2 gave qualitatively similar DNase I footprinting patterns revealing two binding sites: one between positions −236 and −223 (by 5'-deletion mapping, the DNA bases extending to −244 were found to be necessary for bioactivity); and the other between −140 and −117 (ARE-2). Both androgen receptor binding sites are similar to glucocorticoid responsive elements (GRE) with a conserved 5'GTTCT (SEQ ID NO:9), synthetic ARE oligomers were much more efficient competitors in band shift for binding to probasin DNA than those corresponding to the glucocorticoid (GRE; weak competitor) or estrogen (ERE; inactive competitor) responsive elements (Rennie et al., 1993). Further, by homology to the GRE, the PB ARE-1 was defined as −241 to −223 (ATAGCATCTTGTTCTTAGT-SEQ ID NO: 7) whereas ARE-2 encompasses GRE like sequences in −140 to −117 (GTAAAGTACTCCAAGAACCTATTT-SEQ ID NO: 8).

Construction of Chimeric CAT Gene

The plasmid, pPH 1.4, containing the PB 5'-flanking sequence beginning at the Hind III site (−426 bp), exon 1, and part of intron A ending at the Pst I site (Rennie et al., 1993), was digested with Sac I to remove the coding region of exon 1 and intron A. The Sac I site was blunt-ended with Klenow DNA polymerase and ligated to a Bam HI linker. After transformation into E. coli and screening for appropriate clones, the plasmid pBH 500 in the vector pU119 was obtained. The PB-CAT chimeric gene was constructed by inserting the bacterial chloramphenicol acetyl transferase (CAT) gene, prepared from a Bam HI/Bgl II digestion of p-109TK (Cattini et al., 1986), into the Bam HI site of pBH500, creating the −426 to +28 PB sequences adjacent to CAT. This construct also contains the SV40 sequences which provide a 3' intron and polyadenylation and cleavage signals. After transformation into *E. coli* and screening, suitable clones containing the plasmid designated as −426 PB-CAT were isolated. Deletions of −426 PB-CAT were prepared from a Hind III digest followed by a time course treatment with Bal 31 exonuclease (15, 30, 45, 60, and 75 seconds). The Hind III site was reconstituted by ligation to Hind III linkers. After transformation into *E. coli*, clones containing deletion mutants were screened and their plasmid DNAs digested with Hind III and Eco RI to determine fragment sizes by electrophoresis in 1.5% agarose gels. A range of deletion mutants was picked as a result of this enzyme digestion size screening. The original clones were then double digested with Hind III and Bam HI, and the insert isolated after electrophoresis in low melting point agarose gels. Subsequently, the Hind IInI/Bam HI fragments were subcloned into the Hind III and Bam HI sites of an undeleted pUC119 plasmid vector. The amount of PB bp in each construct (FIG. 2) is labelled with a negative and/or positive number from the sequence depicted in FIG. 1. The nucleotide sequences of the construct were confirmed by dideoxy sequencing.

Further PB-CAT chimeric constructs were made by replacing the endogenous PB promoter with the TK gene promoter. The PB fragments were obtained by the appropriate restriction enzyme digest. One construct was made by PCR amplifying the −244 to −96 region using one primer containing a Hind III site at the 5' end and the other primer containing an Xba I site at the 3' end (Rennie et al., 1993). This polymerase chain reaction (PCR) amplified fragment was forced orientation subcloned into Hind III/Xba I TKCAT, generating the chimeric plasmid −243/−96PB-TKCAT. Mutations were made using Muta-Gene Phagmid in vitro mutagenesis kit (Bio-Rad, Mississauga, Ontario, Canada). The nucleotide sequences of all constructs were confirmed by dideoxy sequencing.

Cell Culture and Transfections

HeLa cells were plated at an initial density of $2 \times 10^6/100$ mm dish in Dulbecco's Modified Eagle's Medium (DMEM) supplemented with 10% fetal calf serum (FCS) or 5% FCS and 5% calf serum. The PC-3 cells were plated at an initial density of $8 \times 10^5/100$ mm dish in Minimal Essential Media (MEM) supplemented with 10% FCS. Transient transfection of the HeLa cells with plasmid DNA was performed using a calcium phosphate/DNA precipitation method (Cattini et al., 1986). The cells were treated with 20% glycerol/DMEM for 2 minutes at 6 hours post-transfection and were subsequently grown in DMEM plus 1% charcoal stripped FCS (STR-FCS) with or without dihydrotestosterone (DHT), or dexamethasone (DEX) for 24 or 40 hours before cells were harvested. Transient transfection of PC-3 were performed as outlined for HeLa cells except that the PC-3 cells were grown in MEM plus 5% STR-FCS.

CAT Assays

Cells which had undergone transient transfection were harvested in phosphate buffered saline containing 1 mM EDTA. After centrifugation at 2000×g for 4 min at room temperature, cells were lysed in 0.1M Tris-HCl/0.1% Triton X-100, pH 7.8 for 15 min on ice. Insoluble material was removed by centrifugation at 14,500×g, 15 minutes, at 4° C. The CAT activity in the cell extract was determined by a two-phase fluor diffusion assay (Nachtigal et al., 1989). Also, the DNA was isolated from the insoluble material and 2 µg samples were placed in duplicate on nitrocellulose membrane via slot-blot apparatus and probed with $^{32}$P-labelled CAT insert DNA. Autoradiograms were analyzed by densitometry and all CAT activity data was normalized for transfection efficiency. For transgenic mice, a total cellular extract of each tissue was assayed for CAT activity.

Characterization of the Mechanism of Androgen Action

The PB DNA sequence comprising nucleotides −426 to +28 (FIG. 1) contains the necessary information to obtain androgen regulation, as defined below. The PB-CAT constructs, deletions, and mutations therein, were used to determine the functional significance of ARE-1 and ARE-2.

Due to the lack of appropriate cell lines containing either androgen receptors and/or prostatic in origin, a range of cell lines was tested. The human prostatic cells LNCaP would express and androgen regulate PB-CAT-while HeLa, prostatic DU-145 and PC-3 cells required co-transfection of an androgen receptor expression vector for androgen regulation. The PC-3 human prostatic carcinoma line transiently transfected with the hybrid PB-CAT, co-transfected with the rat androgen receptor expression vector was the standard assay using dihydrotestosterone (DHT) or R1881 (a synthetic androgen). Dexamethasone (DEX), a synthetic glucocorticoid was studied by cotransfecting PC-3 cells with an expression vector for glucocorticoid receptor (GR).

Figure 2B:
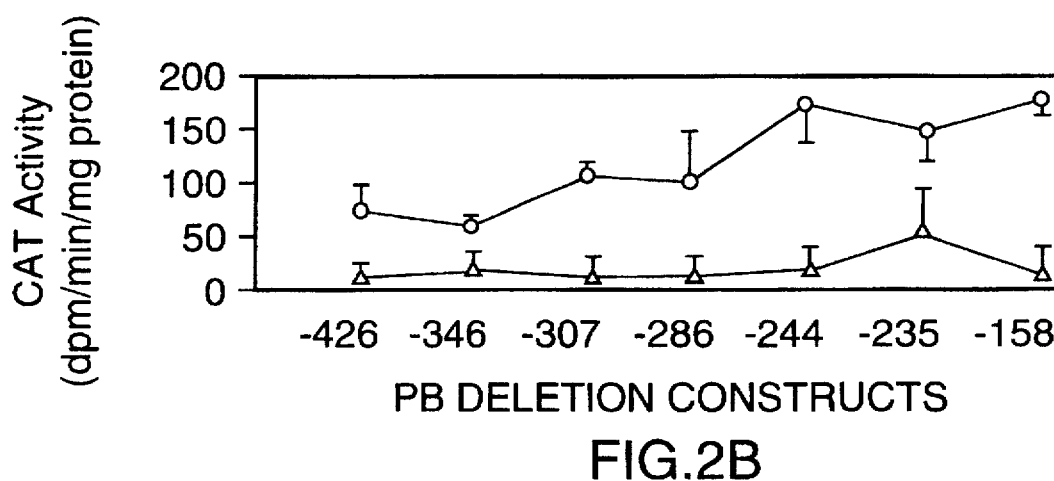

A series of 5'-deletions of PB-CAT DNA were constructed and transfected into PC-3 cells. Deletion of the PB 5'-flanking DNA between 31 426 and −286 resulted in a net increase in androgen inducible CAT activity (FIG. 2). A similar observation was made with cells transfected with GR expression vector and treated with DEX (FIG. 2). The increased activity up to deletion −286 implies that there was a cis-acting silencer upstream. At −286 PB-CAT, the absolute net level of androgen-induced CAT activity (4605 dpm/min/mg protein) as well as a 42-fold increase from basal was higher than the net activity (496 dpm/min/mg protein) and 29-fold induction seen with DEX. At a further deletion to position −244, steroid induction of CAT activity was reduced. Progesterone treatment with cotransfection of the chicken progesterone expression vectors show little activity on −286PB-CAT. The PB AREs preferentially respond to androgens as compared to glucocorticoids and poorly to progestins in both PC-3 and HeLa cells (Table I) which indicates that the PB AREs function as a distinct androgen responsive element rather that as a GRE which is permissive for androgen receptor.

Figure 3:
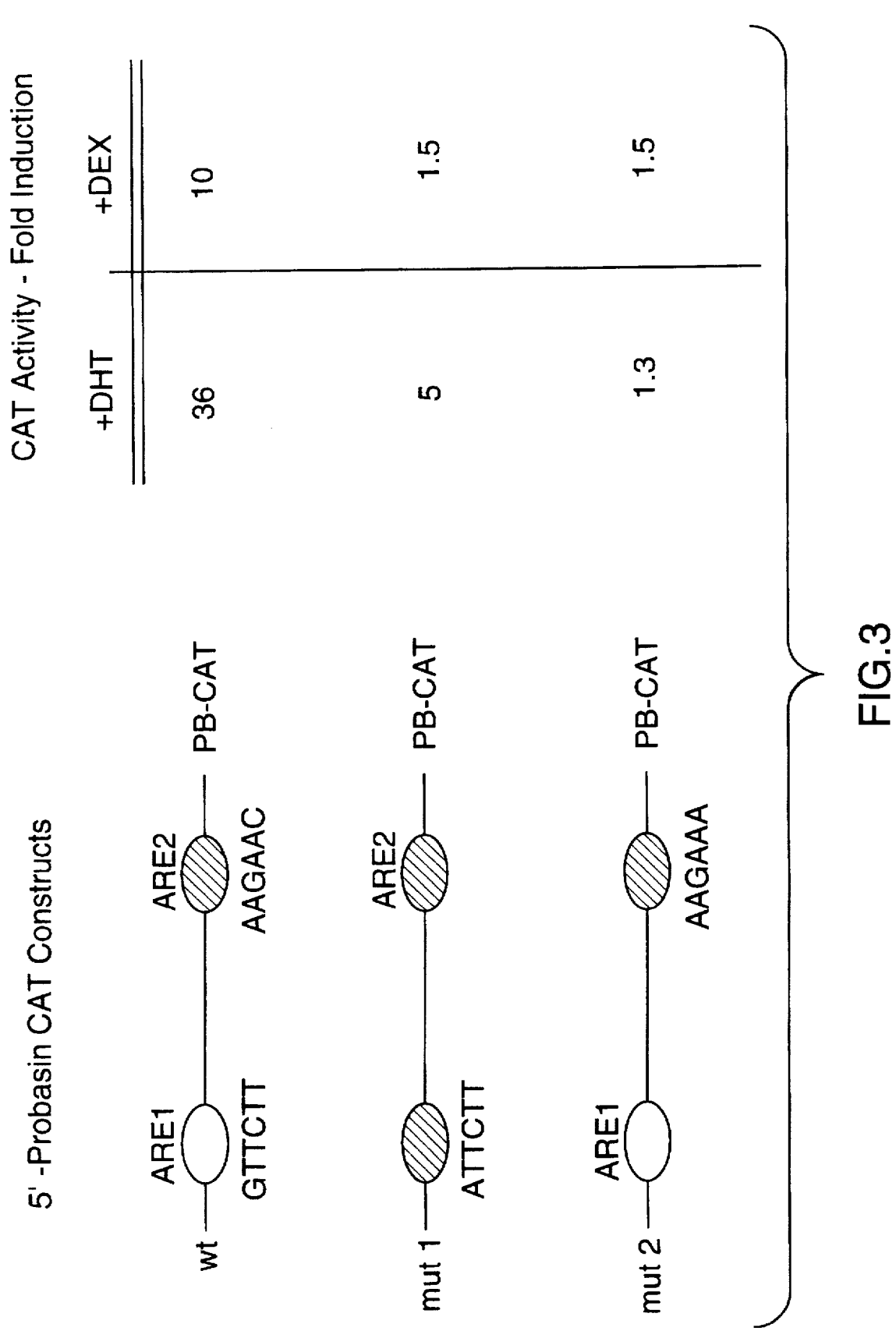
FIG. 3 shows the CAT activity of wild type (wt) AREs (ovals) in −244 PB-CAT compared to single base mutation (hatched ovals) in either ARE-1 (mut 1) or ARE-2 (mut 2). Activities are shown as fold induction from baseline for DHT and DEX with their respective steroid receptor in PC-3 cells.

Further analysis of the 5' and 3' PB flanking regions demonstrates that the two cis-acting DNA elements which bind the androgen receptor, ARE-1 and ARE-2 are both required for androgen induced CAT activity (Rennie et al., 1993). This was demonstrated by making a mutation in ARE-1, at base −231 (G) being changed to A (Mut 1) or within ARE-2, at base −123 (C) being changed to an A (Mut 2) (FIG. 3). Our data also indicates that preferential androgen action requires not only a specific/tight AR binding to the two sites but also interactions with adjacent DNA sequences and proteins. This further mediates cooperativity between AR binding and leads to preferential induction by AR. The two ARE sites function in a cooperative manner for the binding of AR (Table II). AR binds at high affinity when both ARE-1 and ARE-2 are present with the endogenous PB promoter (−286 to +28 bp) as demonstrated by the footprint which occurs at 60 ng of synthetic GST-AR2. Removal of either ARE-1 (−157 to +28 bp) or ARE-2 (−426 to −134 bp)

reduces binding of GST-AR2 to the remaining site (Table II). Single base mutations in ARE-1 (Mut 1) or ARE-2 (Mut-2) reduce steroid induced CAT bioactivity by >95% (FIG. 3) and reduce binding of the GST-AR2 to both AREs (Table II). These two sites require flanking DNA sequences to confer preferential androgen regulation since removal of the endogenous PB promoter (replacing it with thymidine kinase promoter, TK) results in constructs that bind AR only at higher concentrations (Table II) and now are equally inducible by the synthetic glucocorticoid, DEX (Table III). Also, by removing the DNA sequence between ARE-1 and ARE-2 (construct contains ARE-1 placed adjacent to PB position −158 bp which contains the endogenous PB promoter), we see that DEX becomes a potent stimulus to induce CAT activity 21-fold which is similar to DHT induction of 16-fold (Table III).

Figure 4:
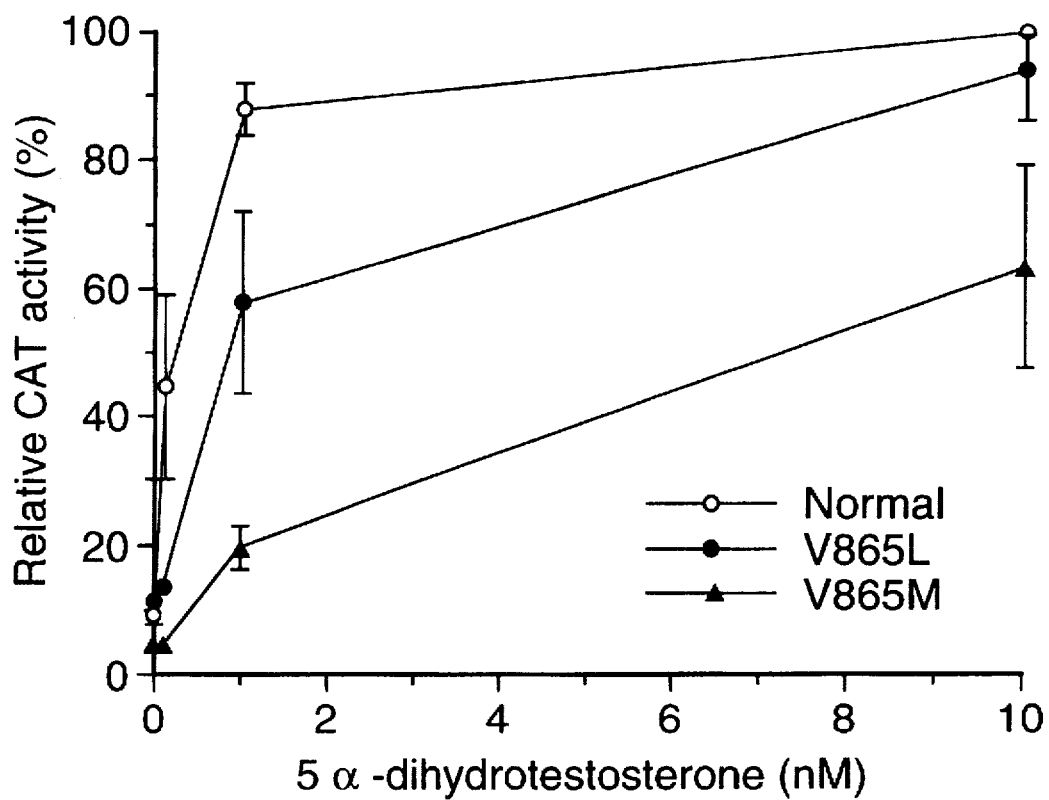
FIG. 4 shows the bioassay of wild type human AR compared to when valine-865 is substituted by methionine (V865M) or leucine (V865L) which results in complete or partial AIS, respectively.

We have demonstrated the utility of the AREs in the −286PB-CAT gene as a bioassay for defective androgen receptor seen in Androgen Insensitivity Syndrome (FIG. 4) (Kazemi-Esfarjani et al., 1993). Differences between the wild type AR and AIS ARs are best recorded a lower concentrations of androgens (1 nM or less) while at high concentrations (10 nM), the wild type AR and V865L show similar response. Our assay also will measure the potency of an anti-androgen material when it is added to compete any androgenic activity. To increase the sensitivity and specificity of the bioassay, two additional improvements have been made.

1) −286 PB-ARE2*CAT: The sequence within ARE-2 was changed by substitution of four bases at −130 to −127 from CCAA with −130 to −127 TACT (SEQ ID NO. 3) or GTCT (SEQ ID NO. 4) resulting in ARE2* (see FIG. 1). These constructs shows an increased response to androgens such that the change gave 100-fold induction compared to wild type −286PB-CAT which gave 36-fold induction. Further, this ARE2* showed an increased response for DEX of 19-fold compared to wild type −286PB-CAT which gave 9.6-fold. The −286 PB-ARE2*CAT also demonstrated that androgen specificity can be separated further from the glucocorticoid inducible effect resulting in enhanced bioactivity and increased sensitivity. For example, androgens plus androgen receptor or plus defective androgen receptor as found in AIS show a greater difference with ARE2* constructs when compared to the wild type −286 PB-CAT (Table IV).

2) (−244/−96)nPB-TK. Although DHT and DEX function equally well and androgen specificity is lost with the replacement of PB promoter region (−96/+28) by TK (either −109 bp or −81 bp TK), the gain in the bioassay has been that the TK promoter functions in all cells tested. In order to regain androgen specificity while keeping the TK promoter, the −244/−96 has been arranged 5' to 3' as repeats adjacent to −109 or −81 TK where both TK promoters function equally well for induction by steroids but the −81 TK starts with a very low basal activity. The CAT gene when replaced by the Luciferase (Luc) reporter increases the sensitivity of the assay (De Wet et al., 1987). The constructs are (−244/−96)nPB-81TKLuc where n equal the number of repeats. When n=2 or n=3, a potent androgen response is obtained with only a small increase as n increases further when 5 µg of DNA construct is transfected (Table V). These constructs show increased sensitivity to measuring the activity of the androgen receptor, of androgens at very low concentrations (Table VI), and of defects in the AR as seen in AIS (Table VII).

Routinely, three repeats (−244/−96 PB) give a >300-fold induction in response to androgens (Table VI and VII) and show specificity for androgens over DEX at very low concentrations of steroids while at high concentrations of steroids, both DHT and DEX show equal activity (Table VI). This indicates the assay is not limited to androgens but also can measure other steroid activities at higher concentrations of these steroids (>1 nM). A combination of either four base change described for ARE2* in each repeat of −244/−96 PB will further increase the sensitivity to steroids.

2) Transgenic non-human eukaryotic animal models for prostatic disease

In order to establish new animals models for prostatic carcinogenesis and benign prostatic hyperplasia, the PB sequence (FIG. 1) can be used to target any gene to the prostate. We have proven that the PB 5'-flanking region contains the necessary sequences for prostatic targeting in transgenic mice by demonstrating that PB will direct prostate specific expression of the bacterial CAT gene (Greenberg et al., 1992a; Greenberg et al., 1992b; Greenberg et al., 1993; Greenberg et al., 1993). Prostate specific expression and androgen regulation in transgenic animals of the PB targeted gene is described.

In vivo studies have demonstrated that the PB promoter targets prostate-specific expression in transgenic mice. Using the −426/+28 PB-CAT construct as the transgene, 5 of 21 pups born following microinjection were identified by PCR as carrying the PB-CAT transgene (4 males, 1 female). Lines were established with the founder transgenic mice and were shown to transmit the same pattern of PB-CAT expression to the prostate of subsequent generations. Three of the male transgenic lines showed prostate-specific CAT expression while no CAT activity was detected in any tissue of one male and the female. Transgenic line #4248 (Table VIII) shows a high level of CAT activity in the prostate while line #4217 shows the lowest level but the same prostate-specific expression of CAT activity. The third male had intermediate CAT levels. The variability in the level of transgenic CAT expression among lines, including the lack of expression in one male founder, may be due to the site of transgene integration. Further characterization of the highly expression transgenic line (#4248) demonstrates extremely high CAT activity in the lateral lobe (Using only 5 ug of tissue extract results in 21% of the substrate being acetylated, while at the usual 25 ug of extract, 89% of the substrate is acetylated). The fact that the PB gene's promoter functions so well is consistent with the high level of expression of the endogenous PB gene in the lateral prostate (8% of the total mRNA). The male accessory organ distribution of CAT activity in the transgenic mouse (true of all three lines, line #4248 in Table IX) closely parallels the endogenous rat PB mRNA levels reported (Matusik et al., 1986). Further, the in situ hybridization and immunohistochemistry of CAT reveal that the PBCAT gene is expressed in the same epithelial cells that was reported for PB mRNA and protein (Spence et al., 1989; Sweetland et al., 1988).

Further, the PBCAT gene demonstrates developmental and androgen regulation of expression. By 7 weeks of age in 3 males of 5 founders mice (4 males, 1 female), the CAT gene was preferentially expressed in the lateral, dorsal, and ventral prostate. Again as the animals age (to 23 week old), only low levels were detected in the anterior prostate and seminal vesicles and no CAT activity was detected in the brain, kidney, spleen, lung, heart, thymus, liver, or testis of any line. However, as the animals aged in line #4248, expression of PB-CAT increased in the ventral prostate up till the last time point checked (23 weeks), decreased in the lateral lobe, showing little change in the dorsal lobe. The CAT activity in the prostate ranged over several logs between the lowest and highest expressing mouse lines, likely due to the site of transgene integration. This expression pattern has been passed over 4 generations. The high expressing male founded line #4248 showed a 70-fold increased prostatic CAT activity between 3 to 7 weeks of age, a time corresponding to sexual maturation. By 7 days after androgen removal (castration of mature males, line #4248), prostatic CAT activity declined (Table X) and could be induced by androgen replacement but not DEX (Table X). In subsequent studies, PB-CAT was coinjected with chicken lysozyme gene matric attachment region, MAR, (McKnight et al., 1992) and cointegration of the MAR and PB-CAT resulted in dorsolateral prostate-specific CAT expression in all three lines examined. With the addition of MAR, no ventral expression was detected in transgenic mice.

This demonstrates the specificity and androgen regulation of the PB 5'-flanking sequences with the CAT reporter transgene in transgenic non-human eukaryotic animals. To enhance the androgen regulation, the ARE2*, repeats of −244/−96 PB, and/or ARE2* placed into repeats of −244/−96 can be added to the −426/+28 PB promoter. To make the promoter responsive to metal ions, such as Zn and Cd, a MT inducible elements, such as used in transgenic animals (Dyer et al., 1989; Iwamoto et al., 1992; Li et al., 1989; Russo et al., 1988; Mayo et al., 1988; Iwamoto et al., 1991) or to make it responsive to glucocorticoids, the GRE sequences, such as seen in the MMTV promoter (Stamp et al., 1992; Lin et al., 1992; Lucchini et al., 1992; Bouchard et al., 1989; Muller et al., 1988; Leder et al., 1986), can be added. The PB 5'-flanking sequence can be used to target any gene to the prostate that may change prostatic function, growth, or cause tumor formation. The targeted genes include large T, TRPM-2, bcl-2, mutated p53, myc, ras, bFGF, TGF-β1, activin, activin receptor, AR, RXR, c-fos, IGFs, IGFBPs, PSA, and int-2. Further, transgenic lines bearing different PB-targets genes can be crossed to develop new lines that show a different incidence or type of tumor development. In this manner, genes important for prostatic tumor growth can be identified. In addition, PB-targeted genes may work in combination with other endogenous genes or newly activated genes to induce tumor growth. The PB transgenic model permits identification of these genes.

3) Cell culture models for prostatic disease.

The transgenic mouse models developed will enable researchers to study and dissect the multistep process of tumorigenesis as it occurs in vivo. These investigations will yield relevant histological and pathological correlates with the known transgenic phenotype in the context of the whole animal. However, whole animal studies are not always adaptable to delineate the various interactions materials, such as hormones, growth factors, attachment factors and cytokines, which affect growth rate, differentiation, metastatic potential and phenotypic expression. In order to address these parameters, a rapid in vitro model for assays can be established. Transgenic animal lines, produced with the PB targets genes which then show prostatic overgrowth or tumor formation, are used as a source of tissue to isolate cells for the establishment of replicative cell cultures (cell lines). Immortalized cells taken from transgenic animals have been successfully used to establish cell culture lines (Larue et al., 1993; Hammang et al., 1990; Martinez de la Escalera et al., 1992; Mellon et al., 1992; von Deimling et al., 1990; Windle et al., 1990; Dalemans et al., 1990; Galiana et al., 1990; Vaux et al., 1988; Efrat et al., 1988; Anonymous, 1991; Tal et al., 1992).

4) Treatment of human benign prostatic hyperplasia and human prostate cancer

The treatment of human disease by gene therapy can be applied to human benign prostatic hyperplasia (hBPH), prostate cancer (CaP), and any disease state of the prostate by using the ability of probasin to target a toxin to prostatic cells. Our studies described in this patent demonstrate that PB directs expression to the transgenic animal prostate and PB directs expression in human prostatic cancer cell lines. Since transgenes coupled to the probasin promoter would be targeted for expression specifically to the prostatic cells, side effect of the therapy on other cell types would be limited. In CaP, stable integration of the PB-targeted transgene into patient chromosomal DNA would not be required since the goal is to kill the cancer cells. Therapy for hBPH may be designed to kill the hyperplastic cells or to integrate the PB-targeted transgene to correct or reduce the hyperplastic growth.

SUMMARY OF DISCLOSURE

In summary of this disclosure, the present invention provides a novel DNA sequence which permits establishment of an assay for androgenic and anti-androgenic materials, transgenic animals and gene therapy for treatment of the prostate.

Features of the present invention described herein and provides hereby include the following:

1. By transient transfected or stably integrated PB sequences coupled to a reporter gene, a bioassay for androgenic materials can be performed in cell culture. The androgenic material is not limited to ligands for the androgen receptor but may include non-steroid pathways that result in androgen action, proteins, DNA and RNA sequences important for androgen action.

2. The transfected cells of feature 1 can be used to bioassay any anti-androgenic material by competition studies with androgenic material. The anti-androgenic material includes receptor ligands, proteins, DNA and RNA sequences, materials the may alter the phosphorylation state, and alter the pathway of androgen action. The anti-androgen material may interfere in the androgen action pathway by direct binding of the ligand to the steroid receptor, it may bind directly to the steroid receptor or PB DNA sequences thus interfering with receptor binding to DNA, RNA, and/or proteins, or it may affect modification of material in the pathway of androgen action.

3. Androgenic and anti-androgenic materials can be assayed by determining their effect on the binding of androgen receptor to PB DNA sequences or to protein complexes bound with the androgen receptor to PB DNA sequences.

4. In transgenic non-human eukaryotic animals, the PB sequences target genes to the male urogenital tract with the highest level of expression in prostatic cells. Gene (s) would be integrated into the chromosome of the animal by introduction at the embryonic stage.

5. In non-human eukaryotic animals, the PB sequences can target genes to the male urogenital tract after injecting DNA via viral or non-viral methods resulting in the highest level of expression in prostatic cells.

6. In animals of feature 4 or 5, the PB promoter regulates expression of gene(s). Transcription via the PB promoter may be further regulated by the addition of enhancer, inducible, or repressor DNA elements.

7. In animals of feature 4 or 5, genes targeted can induce prostatic disease including prostatitis, hyperplasia, urethral obstruction, and prostate cancer to serve as models.

8. From animals of feature 7, cells can be isolated from prostatic tissue to establish cell lines.

9. In animals of feature 4 or 5 or cell lines of feature 8, therapies may be tested to develop new drugs including new approached to gene therapy.

10. The predisposition of animals of features 4 or 5 or cell lines of feature 8 for prostatic disease can be used to test materials that have protective value against the development or progression of prostatic disease. A lower incidence of prostatic tumor development would demonstrate a protective value of an agent.

11. The predisposition of animals of feature 4 or 5 or cell lines of feature 8 to prostatic disease increases the sensitivity to measure materials for carcinogenicity. Transgenic animals lines or cell culture lines can be selected that have a low susceptibility of developing prostatic tumors and treated with a potential carcinogen over a range of doses. Further, lines which develop tumors rapidly would increase the sensitivity of the test to weak carcinogens. A carcinogen should show an increase in tumor development and or progression over controls.

12. In animals (transgenic as well as non-transgenic), the PB sequences can be used as a model to develop methods for new gene therapies by the delivery of genes which express toxins or convert drugs into toxic substances in normal prostatic, hyperplastic, and cancerous cells.

13. In humans, the PB sequences can be used in gene therapy to target genes to the male urogenital tract, benign prostatic hyperplasia, and prostatic cancer. Targeted genes can express toxins or converted drugs into toxic substances thereby inhibiting the growth or killing prostatic cells.

Modifications are possible within the scope of this invention.

REFERENCES

Adams, J. M., Harris, A. W., Pinkert, C. A., et al. *Nature* 318:533, 1985.

Adler, A. J., Scheller, A., Hoffman, Y. and Robins, D. M. *Molecular Endocrinology* 5:1587, 1991.

Adler, A. J., Danielsen, M. and Robins, D. M. *Proceedings of the National Academy of Sciences of the United States of America* 89:11660, 1992.

Allan, G. F., Tsai, S. Y., O'Malley, B. W. and Tsai, M. J. *Bioessays* 13:73, 1991.

Allison, J., Zhang, Y. L. and Parker, M. G. *Molecular & Cellular Biology* 9:2254, 1989.

Anderson, W. F. *Science* 256:808, 1992.

Anonymous, *Immunol Ser;* 41:1–396 1988.

Anonymous, *Workshop on Neoplastic Transformation in Human Cell Systems In Vitro: Mechanisms of Carcinogenesis.* Apr. 25–26, 1991.

Anonymous, *Raven Press Ser Mol Cell Biol;* 1:1–364 1992.

Armbruster, D. A. *Clin Chem* 39:181, 1993.

Bautch, V. L. *Molecular Biology & Medicine* 6:309, 1989.

Beato, M. *Cell* 56:335, 1989.

Bookstein, R. and Allred, D. C. *Cancer* 71:1179, 1993.

Borrelli, E., Sawchenko, P. E. and Evans, R. M. *Proceedings of the National Academy of Sciences of the United States of America* 89:2764, 1992.

Bouchard, L., Lamarre, L., Tremblay, P. J. and Jolicoeur, P. *Cell* 57:931, 1989.

Breuer, M., Slebos, R., Verbeek, S., van Lohuizen, M., Wientjens, E. and Berns, A. *Nature* 340:61, 1989.

Brinkmann, A. O., Kuiper, G. G., Ris-Stalpers, C., et al. *Journal of Steroid Biochemistry & Molecular Biology* 40:349, 1991.

Brinkmann, A. O., Jenster, G., Kuiper, G. G., et al. *Journal of Steroid Biochemistry & Molecular Biology* 41:361, 1992a.

Brinkmann, A. O. and Trapman, J. *Cancer Surveys* 14:95, 1992b.

Burck, K. B., Liu, E. T. and Larrick, J. W. *Oncogenes: An Introduction to the Concept of Cancer Genes.* New York. Springer, 300 p., 1988.

Butel, J. S., Sepulveda, A. R., Finegold, M. J. and Woo, S. L. *Intervirology* 31:85, 1990.

Buttyan, R. and Slawin, K. *Cancer & Metastasis Reviews* 12:11, 1993.

Callahan, R. and Campbell, G. *Journal of the National Cancer Institute* 81:1780, 1989.

Carter, B. S., Epstein, J. I. and Isaacs, W. B. *Cancer Research* 50:6830, 1990a.

Carter, B. S., Ewing, C. M., Ward, W. S., et al. *Proceedings of the National Academy of Sciences of the United States of America* 87:8751, 1990b.

Cato, A. C. B., Henderson, D. and Ponta, H. *Embo Journal* 6:363, 1987.

Cattini, P. A., Peritz, L. N., Anderson, T. R., Baxter, J. D. and Eberhardt, N. L. *DNA* 5:503, 1986.

Claessens, F., Celis, L., Peeters, B., Heyns, W., Verhoeven, G. and Rombauts, W. *Biochemical & Biophysical Research Communications* 164:833, 1989a.

Claessens, F., Dirckx, L., Delaey, B., et al. *Journal of Molecular Endocrinology* 3:93, 1989b.

Claessens, F., Rushmere, N., Celis, L., Peeters, B., Davies, P. and Rombauts, W. *Biochemical Society Transactions* 18:561, 1990a.

Claessens, F., Rushmere, N. K., Davies, P., Celis, L., Peeters, B. and Rombauts, W. A. *Molecular & Cellular Endocrinology* 74:203, 1990b.

Claessens, F., Celis, L., De Vos, P., et al. *Biochemical & Biophysical Research Communications* 191:688, 1993.

Culotta, E. *Science* 260:914, 1993.

Culver, K. N. and et al., *Science* 257:99, 1992.

Dalemans, W., Perraud, F., Le Meur, M., Gerlinger, P., Courtney, M. and Pavirani, A. *Biologicals* 18:191, 1990.

Darbre, P., Page, M. and King, R. J. B. *Molecular & Cellular Biochemistry* 6:2847, 1986.

Davies, K. *Nature* 361:5, 1993.

De Bellis, A., Quigley, C. A., Cariello, N. F., et al. *Molecular Endocrinology* 6:1909, 1992.

De Vos, P., Claessens, F., Winderickx, J., et al. *Journal of Biological Chemistry* 266:3439, 1991.

De Wet, J. R., Wood, K. V., Deluca, M. and Helinski, D. R. *Molecular & Cellular Biochemistry* 7:725, 1987.

Denison, S. H., Sands, A. and Tindall, D. J. *Endocrinology* 124:1091, 1989.

Dodd, J. G., Sheppard, P. C. and Matusik, R. J. *Journal of Biological Chemistry* 258:10731, 1983.

Dodd, J. G., Kreis, C., Sheppard, P. C., Hamel, A. and Matusik, R. J. *Molecular & Cellular Endocrinology* 47:191, 1986.

Dodd, J. G., Morris, G., Miller, T. L., et al. Oncogenes and the prostate. In: *The prostate as an endocrine gland,* edited by Farnsworth, W. E. and Ablin, R. J. Florida: CRC press, 1990, p. 49–66.

Dodd, J. G., Paraskevas, M. and McNicol, P. J. *J.Urol.* 149:400, 1993.

Dubois, N., Bennoun, M., Allemand, I., et al. *Journal of Hepatology* 13:227, 1991.

Dyer, K. R. and Messing, A. *American Journal of Pathology* 135:401, 1989.

Efrat, S., Linde, S., Kofod, H., et al. *Proceedings of the National Academy of Sciences of the United States of America* 85:9037, 1988.

Eva, A., Graziani, G., Zannini, M., Merin, L. M., Khillan, J. S. and Overbeek, P. A. *New Biologist* 3:158, 1991.

Evans, R. M. *Science* 240:889, 1988.

Feigner, P. L. *Laboratory Investigation* 68:1, 1993.

Fenjves, E. S. and et al., *Proceedings of the National Academy of Sciences of the United States of America* 86:8803, 1989.

Fleming, W. H., Hamel, A., MacDonald, R., et al. *Cancer Research* 46:1535, 1986.

Folkman, J., Watson, K., Ingber, D. and Hanahan, D. *Nature* 339:58, 1989.

French, F. S., Lubahn, D. B., Brown, T. R., et al. *Recent Progress In Hormone Research* 46:1, 1990.

Friedmann, T. *Cancer* 70:1810, 1992.

Galiana, E., Borde, I., Marin, P., et al. *Journal of Neuroscience Research* 26:269, 1990.

Greenberg, M. N., Dodd, J. G., Duckworth, M. L., Rosen, J. M. and Matusik, R. J. *The Endocrine Society* Jun. 9–11: Abstract 1206, 1993. (Abstract)

Greenberg, N. M., Matusik, R. J. and Rosen, J. M. *NIDDKD* Sep. 11–13:1992a. (Abstract)

Greenberg, N. M., Rosen, J. M. and Matusik, R. J. *Prouts Neck* Oct. 15–18:1992b. (Abstract)

Greenberg, N. M., Dodd, J. G., Duckworth, M. L., Rosen, J. M. and Matusik, R. J. *SBUR* May 15:1993. (Abstract)

Ham, J., Thomson, A., Needham, M., Webb, P. and Parker, M. *Nucleic Acids Research* 16:5263, 1988.

Hamaguchi, K. and Leiter, E. H. *Diabetes* 39:415, 1990.

Hammang, J. P., Baetge, E. E., Behringer, R. R., Brinster, R. L., Palmiter, R. D. and Messing, A. *Neuron* 4:775, 1990.

Hanahan, D. *Oncogenes and Growth Control*. Kahn P. et al, eds. New York, Springer-Verlag, p.349–63, 1986.

Harris, S. E., Harris, M. A., Johnson, C. M., et al. *Journal of Biological Chemistry* 265:9896, 1990.

He, W. W., Kumar, M. V. and Tindall, D. J. *Nucleic Acids Research* 19:2373, 1991.

Heyns, W., Peeters, B., Mous, J., Rombauts, W. and DeMoor, P. *European Journal of Biochemistry* 89:181, 1978.

Ho, K. C., Snoek, R., Quarmby, V., et al. *Biochemistry* 28:6367, 1989.

Ho, K. C., Quarmby, V. E., French, F. S. and Wilson, E. M. *Journal of Biological Chemistry* 267:12660, 1992.

Hockenbery, D. *Proc Annu Meet Am Assoc Cancer Res;* 33:A585-6 1992.

Hurst, H. and Parker, M. G. *Embo Journal* 2:769, 1983.

Hyde, S. C., Gill, D. R., Higgins, C. F., et al. *Nature* 362:250, 1993.

Ichikawa, T., Ichikawa, Y., Dong, J., et al. *Cancer Research* 52:3486, 1992.

Imperato-McGinley, J., Ip, N. Y., Gautier, T., et al. *American Journal of Medical Genetics* 36:104, 1990.

Isaacs, W. B. and Carter, B. S. *Cancer Surveys* 11:15, 1991a.

Isaacs, W. B., Carter, B. S. and Ewing, C. M. *Cancer Research* 51:4716, 1991b.

Iwamoto, T., Takahashi, M., Ito, M., et al. *Embo Journal* 10:3167, 1991.

Iwamoto, T., Takahashi, M., Ohbayashi, M. and Nakashima, I. *Experimental Cell Research* 200:410, 1992.

Kazemi-Esfarjani, P., Beitel, L., Trifiro, M., et al. *Molecular Endocrinology* 7:37, 1993.

Klein-Hitpass, L., Schorpp, M., Wagner, U. and Ryffel, G. U. *Cell* 46:1053, 1986.

Knight, K. L., Spieker-Polet, H., Kazdin, D. S. and Oi, V. T. *Proceedings of the National Academy of Sciences of the United States of America* 85:3130, 1988.

Kuiper, G. G., de Ruiter, P. E., Trapman, J., Boersma, W. J., Grootegoed, J. A. and Brinkmann, A. O. *Biochemical Journal* 291:95, 1993.

La Spada, A. R., Wilson, E. M., Lubahn, D. B., Harding, A. E. and Fischbeck, K. H. *Nature* 352:77, 1991.

Langdon, W. Y., Harris, A. W. and Cory, S. *Oncogene Research* 4:253, 1989.

Larue, L., Dougherty, N., Bradl, M. and Mintz, B. *Oncogene* 8:523, 1993.

Leder, A., Pattengale, P. K., Kuo, A., Stewart, T. A. and Leder, P. *Cell* 45:485, 1986.

Leder, P. *Animal Model for Benign Prostatic Disease:* Patent WO 90/09443, World Intellectual Property Organization, 1990. (UnPub)

Li, S., Klein, E. S., Russo, A. F., Simmons, D. M. and Rosenfeld, M. G. *Proceedings of the National Academy of Sciences of the United States of America* 86:9778, 1989.

Lin, T. P., Guzman, R. C., Osborn, R. C., Thordarson, G. and Nandi, S. *Cancer Research* 52:4413, 1992.

Lubahn, D. B., Brown, T. R., Simental, J. A., et al. *Proceedings of the National Academy of Sciences of the United States of America* 86:9534, 1989.

Lucchini, F., Sacco, M. G., Hu, N., et al. *Cancer Letters* 64:203, 1992.

Martinez de la Escalera, G., Choi, A. L. and Weiner, R. I. *Proceedings of the National Academy of Sciences of the United States of America* 89:1852, 1992.

Matsui, Y., Halter, S. A., Holt, J. T., Hogan, B. L. and Coffey, R. J. *Cell* 61:1147, 1990.

Matusik, R. J., Kreis, C., McNicol, P., et al. *Biochemistry & Cell Biology* 64:601, 1986.

Matusik, R. J., Fleming, W. H., Hamel, A., et al. *Progress In Clinical & Biological Research* 239:91, 1987.

Matzuk, M. M., Finegold, M. J., Su, J.-G. J., Hsueh, A. J. W. and Bradley, A. *Nature* 360:313, 1992.

Mayo, K. E., Hammer, R. E., Swanson, L. W., Brinster, R. L., Rosenfeld, M. G. and Evans, R. M. *Molecular Endocrinology* 2:606, 1988.

McKnight, R. A., Shamay, A., Sankaran, L., Wall, R. J. and Hennighausen, L. *Proceedings of the National Academy of Sciences of the United States of America* 89:6943, 1992.

McNicol, P. J. and Dodd, J. G. *Journal of Clinical Microbiology* 28:409, 1990a.

McNicol, P. J. and Dodd, J. G. *Canadian Journal of Microbiology* 36:359, 1990b.

McNicol, P. J. and Dodd, J. G. *J.Urol.* 145:850, 1991.

Mellon, P. L., Wetsel, W. C., Windle, J. J., et al. *Ciba Foundation Symposium* 168:104, 1992.

Montgomery, B. T., Young, C. Y., Bilhartz, D. L., et al. *Prostate* 21:63, 1992.

Morris, G. L. and Dodd, J. G. *J.Urol.* 143:1272, 1990.

Morton, R. A., Isaacs, J. T. and Isaacs, W. B. *Prostate* 17:327, 1990.

Mougneau, E., Meneguzzi, G. and Cuzin, F. *Genes and Signal Transduction in Multistage Carcinogenesis*. Colburn N.H., ed., New York, Marcel Dekker, p. 221–9, 1989.

Mukhopadhyay, T. and et al., *Cancer Research* 51:1744, 1991.

Muller, W. J., Sinn, E., Pattengale, P. K., Wallace, R. and Leder, P. *Cell* 54:105, 1988.

Muller, W. J., Lee, F. S., Dickson, C., Peters, G., Pattengale, P. and Leder, P. *Embo Journal* 9:907, 1990.

Muller, W. J. *Cancer & Metastasis Reviews* 10:217, 1991.
Mulligan, R. C. *Science* 260:926, 1993.
Murphy, B. C., Pienta, K. J. and Coffey, D. S. *Prostate* 20:29, 1992.
Nachtigal, N. W., Nickel, B. E., Klassen, M. E., Zhang, W., Eberhardt, N. L. and Cattini, P. A. *Nucleic Acids Research* 17:4327, 1989.
Newmark, J. R., Hardy, D. O., Tonb, D. C., et al. *Proceedings of the National Academy of Sciences of the United States of America* 89:6319, 1992.
Parker, M. G., White, R. and Williams, J. G. *Journal of Biological Chemistry* 255:6996, 1980.
Parker, M. G. and Needham, M., . In: *Regulation of androgen action*, edited by Bruchovsky, N., Chapdelaine, A. and Neumann, F. Berlin: Congressdruck R. Bruckner, 1985, p. 175–178.
Parker, M. G., Webb, P. Mills, J. S., Needham, M. and White, R. *Journal of Steroid Biochemistry* 30:47, 1988.
Pawson, T. *Dev Oncol;* 51:155–71 1987.
Peehl, D. M. *Cancer* 71:1159, 1993.
Perry, S. T., Viskochil, D. H., Ho, K.-C., et al. In: *Regulation of androgen action*, edited by Bruchovsky, N., Chapdelaine, A. and Neumann, F. Berlin: Congressdruck R. Bruckner, 1985, p. 167–173.
Pienta, K. J., Isaacs, W. B., Vindivich, D. and Coffey, D. S. *J.Urol.* 145:199, 1991.
Power, R. F., Mani, S. K., Codina, J., Conneely, O. M. and O'Malley, B. W. *Science* 254:1636, 1991.
Quigley, C. A., Evans, B. A., Simental, J. A., et al. *Molecular Endocrinology* 6:1103, 1992.
Rennie, P. S., Bowden, J. F., Freeman, S. N., et al. *Molecular Endocrinology* 3:703, 1989.
Rennie, P. S., Bruchovsky, N., Leco, K. J., et al. *Molecular Endocrinology* 7:23, 1993.
Reynolds, R. K., Hoekzema, G. S., Vogel, J., Hinrichs, S. H. and Jay, G. *Proceedings of the National Academy of Sciences of the United States of America* 85:3135, 1988.
Riegman, P. H., Vlietstra, R. J., van der Korput, J. A., Brinkmann, A. O. and Trapman, J. *Molecular Endocrinology* 5:1921, 1991.
Rindi, G., Efrat, S., Ghatei, M. A., Bloom, S. R., Solcia, E. and Polak, J. M. *Virchows Archiv—A, Pathological Anatomy & Histopathology* 419:115, 1991.
Ris-Stalpers, C., Kuiper, G. G., Faber, P. W., et al. *Proceedings of the National Academy of Sciences of the United States of America* 87:7866, 1990.
Ris-Stalpers, C., Trifiro, M. A., Kuiper, G. G., et al. *Molecular Endocrinology* 5:1562, 1991.
Roche, P. J., Hoare, S. A. and Parker, M. G. *Molecular Endocrinology* 6:2229, 1992.
Rushmere, N. K., Claessens, F., Peeters, B., Rombauts, W. and Davies, P. *Biochemical Society Transactions* 18:560, 1990 .
Russo, A. F., Crenshaw, E. B., Lira, S. A., Simmons, D. M., Swanson, L. W. and Rosenfeld, M. G. *Neuron* 1:311, 1988.
Sandgren, E. P., Quaife, C. J., Pinkert, C. A., Palmiter, R. D. and Brinster, R. L. *Oncogene* 4:715, 1989.
Sandgren, E. P., Luetteke, N. C., Qiu, T. H., Palmiter, R. D., Brinster, R. L. and Lee, D. C. *Molecular & Cellular Biology* 13:320, 1993.
Schechter, J., Windle, J. J., Stauber, C. and Mellon, P. L. *Neuroendocrinology* 56:300, 1992.
Scheidereit, C., Westphal, H. M., Carlson, C., Bosshard, H. and Beato, M. *DNA* 5:383, 1986.
Shemshedini, L., Ji, J. W., Brou, C., Chambon, P. and Gronemeyer, H. *Journal of Biological Chemistry* 267:1834, 1992.
Short, M. P. and et al., *Journal of Neuroscience Research* 27:427, 1990.
Shrahle, U., Klock, G. and Schutz, G. *Proceedings of the National Academy of Sciences of the United States of America* 84:7871, 1987.
Simental, J. A., Sar, M. and Wilson, E. M. *Journal of Steroid Biochemistry & Molecular Biology* 43:37, 1992.
Sinkovics, J. G. *Critical Reviews in Oncology-Hematology* 11:87, 1991.
Skalnik, D. G., Dorfman, D. M., Williams, D. A. and Orkin, S. H. *Molecular & Cellular Biochemistry* 11:4518, 1991.
Smith, D. F. and Toft, D. O. *Molecular Endocrinology* 7:4, 1993.
Spence, A. M., Sheppard, P. C., Davie, J. R., et al. *Proceedings of the National Academy of Sciences of the United States of America* 86:7843, 1989.
Stamp, G., Fantl, V., Poulsom, R., et al. *Cell Growth & Differentiation* 3:929, 1992.
Stefaneanu, L., Rindi, G., Horvath, E., Murphy, D., Polak, J. M. and Kovacs, K. *Endocrinology* 130:1789, 1992.
Strange, R. and Cardiff, R. D. *Dev Oncol;* 58:1–14 1990.
Sweetland, R., Sheppard, P. C., Dodd, J. G. and Matusik, R. *J. Molecular & Cellular Biochemistry* 84:3, 1988.
Tal, M., Thorens, B., Surana, M., et al. *Molecular & Cellular Biology* 12:422, 1992.
Tan, J., Marschke, K. B., Ho, K. C., Perry, S. T., Wilson, E. M. and French, F. S. *Journal of Biological Chemistry* 267:7958, 1992.
Thompson, T. C., Truong, L. D., Timme, T. L., et al. *Cancer* 71:1165, 1993.
Tolstoshev, P. and Anderson, W. F. Gene transfer techniques in human gene therapy. In: *Genome Research in Molecular Medicine and Virology*, Academic Press, Inc., 1993,
Tutrone, R. F., Jr., Ball, R. A., Ornitz, D. M., Leder, P. and Richie, J. P. *J Urol* 149:633, 1993.
Umesono, K., Giguere, V., Glass, C. K., Rosenfeld, M. G. and Evans, R. M. *Nature* 336:262, 1988.
Vaux, D. L., Cory, S. and Adams, J. M. *Nature* 335:440, 1988.
Veldscholte, J., Ris-Stalpers, C., Kuiper, G. G., et al. *Biochemical & Biophysical Research Communications* 173:534, 1990.
Veldscholte, J., Berrevoets, C. A., Brinkmann, A. O., Grootegoed, J. A. and Mulder, E. *Biochemistry* 31:2393, 1992a.
Veldscholte, J., Berrevoets, C. A., Ris-Stalpers, C., et al. *Journal of Steroid Biochemistry & Molecular Biology* 41:665, 1992b.
von Deimling, A., Aguzzi, A., Kleihues, P., Land, H. and Wiestler, O. D. *Verhandlungen Der Deutschen Gesellschaft Fur Pathologie* 74:432, 1990.
Von der Ahe, D., Pearson, D., Nakagawa, J., Rajput, B. and Nagamine, Y. *Nucleic Acids Research* 16:7527, 1993.
Windle, J. J., Weiner, R. I. and Mellon, P. L. *Molecular Endocrinology* 4:597, 1990.
Wooster, R., Mangion, J., Eeles, R., et al. *Nature Genetics* 2:132, 1992.
Yamamura, K. *Gan To Kagaku Ryoho* 16:733, 1989.
Yarbrough, W. G., Quarmby, V. E., Simental, J. A., et al. *Journal of Biological Chemistry* 265:8893, 1990.
Young, C. Y., Andrews, P. E., Montgomery, B. T. and Tindall, D. J. *Biochemistry* 31:818, 1992.
Zhu N., Liggitt D., Liw Y., Debs R. "Systemic Gene Expression after Intravenous DNA Delivery into Adult Mice", Science 261:209–211, 1993.

TABLE I

Hormonal Induction of PB-CAT

| Cell Type Used | Type of Steroid Receptor Cotransfected with PB-CAT | CAT Activity (dpm/min/mg protein) | | |
|---|---|---|---|---|
| | | −Steriod | +Steroid | Net |
| HeLa | Androgen | 1.5 ± 0.8 | 17 ± 5 | 15.5 |
| | Glucocorticoid | 0.9 ± 0.4 | 17 ± 3 | 17.1 |
| | Progestin* | 95 ± 26 | 68 ± 6 | 0.0 |
| PC-3 | Androgen | 105 ± 21 | 884 ± 105 | 779 |
| | Glucocorticoid | 17 ± 6 | 72 ± 8 | 55 |
| | Progestin* | 29 ± 10 | 115 ± 9 | 86 |

CAT activity is expressed as mean ± SEM for n > 3
*Transfection with −286 PB-CAT rather than −426 PB-CAT

TABLE II

Appearance of Footprint with AR (ng) on the Probasin Promoter

| PB Fragment (bp) | ARE-1 | ARE-2 |
|---|---|---|
| −286 to +28 | 60 ng | 60 ng |
| −426 to −134 | 200 ng | ARE-2 absent |
| −157 to +28 | ARE-1 absent | 100 ng |
| −244 to −96 | 200 ng | 200 ng |
| Mut 1 (−286 to +28) | suggestive* | 200 ng |
| Mut 2 (−286 to +28) | suggestive* | 200 ng |

Mut 1 contains a mutation in ARE-1 that deceases DHT induced CAT bioactivity by >95%
Mut 2 contains a mutation in ARE-2 that deceases DHT induced CAT bioactivity by >95%
*Suggestive indicates that a weak footprint occurs at >400 ng GST-AR2 but always lacks the complete "white out" appearance seen in all other AR footprints.

TABLE III

Bioactivity and Specificity for AR Depends upon both AREs and adjacent DNA Sequences in the PB Fragment

| CAT Construct with either PB* or TK promoter | CAT Activity (dpm/min/mg protein) | | | | | |
|---|---|---|---|---|---|---|
| | −DHT | +DHT | Fold | −DEX | +DEX | Fold |
| −244/+28 PB-CAT | 5.9 | 288 | 49 | 6.2 | 55.5 | 9 |
| −158/+28 PB-CAT | 6.3 | 8.5 | 1.4 | 6.0 | 7.7 | 1.2 |
| (ARE-1) −158/+28 PB-CAT | 6.1 | 108 | 18 | 6.2 | 131 | 21 |
| −244/−265 PB TKCAT | 4.8 | 5.4 | 1.1 | 7.4 | 10.2 | 1.3 |
| −244/−96 PB TKCAT | 6.7 | 410 | 61 | 7.0 | 672 | 96 |

*PB denotes the fragment of probasin flanking DNA.
(ARE-1) refers to the precise sequence placed adjacent to −158 PB-CAT. Fold refers to the increase when steroid is added.

TABLE IV

A Four Base Pair Change in ARE-2 Increases the Sensitivity for Altered Androgen Receptor Seen in AIS

| DNA Construct | −286 PB-CAT | −286 PB-ARE2*CAT |
|---|---|---|
| wild type hAR | 50^ | 177^ |
| V865L hAR | 49^ | 122^ |
| V865M hAR | 42^ | 49^ |

^CAT activity expressed as dpm/min/mg protein. Background CAT activity without androgens is 4.2. Bioassay shown is induced levels with 10 nM DHT.

TABLE V

Repeats of a PB Fragment Containing both ARE-1 and ARE-2

| (−244 to −96)n PB adjacent −81 TK-Luc* | Luc Activity Relative Light Units (RLU) × $10^6$ per min/mg protein | | |
|---|---|---|---|
| | −DHT | +DHT 10 nM | Fold |
| n = 1 | 0.07 | 1.31 | 18 |
| n = 2 | 0.09 | 14.5 | 161 |
| n = 3 | 0.09 | 27.7 | 308 |
| n = 4 | 0.08 | 23.7 | 296 |
| n = 5 | 0.09 | 26.2 | 290 |

*The −81 TK-Luc vector when tested as a control showed only a 1.8 increase with the addition of DHT. All repeats of PB are placed adjacent to each other in the same 5'-3' direction as wild type probasin.

TABLE VI

Repeats of the PB AREs Increase Sensitivity to Low Levels of Androgens

| Agent Tested | | (−244 to −96)n PB −81 TK-Luc | | |
|---|---|---|---|---|
| Steroid* | Concentration | n = 1 | n = 2 | n = 3 |
| R1881 | 1 nM | 11 | 230 | 245 |
| DEX | 1 nM | 3 | 39 | 130 |
| R1881 | 0.1 nM | 9 | 172 | 251 |
| DEX | 0.1 nM | 1.1 | 6 | 18 |
| R1881 | 0.01 nM | 2 | 15 | 24 |
| DEX | 0.01 nM | 0.8 | 1.1 | 1.1 |

*The steroids are R1881 a synthetic androgen and DEX a synthetic glucocorticoid. Data is expressed as fold change from baseline when steroid is added.

TABLE VII

Repeats of the PB AREs Increase Sensitivity to Defects in the AR as seen in AIS

| DNA Construct | (−244 to −96)n PB −81 TK-Luc | | |
|---|---|---|---|
| | n = 1 | n = 2 | n = 3 |
| wild type hAR | 13.6 | 256 | 832 |
| V865L hAR | 11.6 | 146 | 375 |
| V865M hAR | 6 | 54 | 103 |

Data is presented as fold increase of Luc activity from baseline with the addition of 10 nM DHT.

TABLE VIII

Expressed CAT Activity in PB-CAT Trangenic Mouse Line #4248

| TISSUE | CAT ACTIVITY* |
|---|---|
| Brain | 0.08 |
| Kidney | 0.07 |
| Spleen | 0.09 |
| Lung | 0.07 |
| Heart | 0.09 |
| Thymus | 0.15 |
| Liver | 0.12 |
| Testis | 0.13 |
| Seminal Vesicle | 1.01 |
| Lateral Prostate | 37.69 |
| Dorsal Prostate | 2.32 |
| Ventral Prostate | 8.35 |
| Anterior Prostate | 0.23 |

*CAT activity is expressed as conversion of substrate in pmol/hr/mg protein.

TABLE IX

Relative Concentration (PerCent) of Expressed mRNAs in Various Tissues

| TISSUE | ENDOGENOUS RAT PROBASIN | TRANSGENIC MOUSE PB-CAT |
|---|---|---|
| Lateral Prostate | 100 | 100 |
| Dorsal Prostate | 33 | 6 |
| Ventral Prostate | 4 | 22 |
| Anterior Prostate | 14 | 0.6 |
| Seminal Vesicle | 2 | 2.7 |
| Testis | ND* | ND |
| Brain | ND | ND |

TABLE IX-continued

Relative Concentration (PerCent) of Expressed mRNAs in Various Tissues

| TISSUE | ENDOGENOUS RAT PROBASIN | TRANSGENIC MOUSE PB-CAT |
|---|---|---|
| Heart | ND | ND |
| Liver | ND | ND |

*ND = Not Detected

TABLE X

Hormonal Regulation of PB-CAT Expression in Transgenic Mice: Line 4248

| TREATMENT | LATERAL PROSTATE | DORSAL PROSTATE | VENTRAL PROSTATE |
|---|---|---|---|
| Intact: 8 weeks old | 10,212 ± 4,897 | 2,539 ± 812 | 7,905 ± 1,971 |
| Intact: 9 weeks old | 12,083 ± 3,168 | 2,346 ± 630 | 11,787 ± 1,782 |
| Castrated for 7 Days | 529 ± 600 | 374 ± 91 | 218 ± 173 |
| Castrated for 10 Days | 1,364 ± 606 | 224 ± 261 | 2,061 ± 533 |
| Castrated for 7 Days + Test for 3 Days | 8,289 ± 1,855 | 1,222 ± 569 | 7,553 ± 4,075 |
| Castrated for 7 Days + DEX for 3 Days | 1,646 ± 832 | 187 ± 66 | 1,435 ± 228 |

CAT activity is expressed as dpm/min/mg protein ± standard error. Test = testosterone; DEX = dexamethasone

I claim:

1. An isolated DNA molecule comprising the 5'-flanking region of the rat probasin gene which contains at least one androgen responsive element, said 5'-flanking region being contained within the DNA sequence shown in FIG. 1 (SEQ ID NO:1) and being effective to direct prostate-specific expression of a heterologous gene in a prostate-bearing animal under androgen regulation.

2. An isolated DNA molecule comprising the sequence from –426 to +28 bp of the DNA sequence shown in FIG. 1 (1–454 bp of SEQ ID NO: 1) and effective to direct prostate-specific expression of a heterologous gene to the prostate.

3. An isolated DNA molecule comprising the sequence from –426 to +1 bp of the DNA sequence shown in FIG. 1 (1–428 bp of SEQ ID NO: 1) effective to direct prostate-specific expression of a heterologous gene to the prostate.

4. An isolated DNA molecule comprising a 5'-flanking region of the rat probasin gene and which contains two androgen responsive elements, said 5'-flanking region being contained within the DNA sequence shown in FIG. 1 (SEQ ID NO: 1) and being effective to direct prostate-specific expression of a heterologous gene in a prostate-bearing animal under androgen regulation.

5. The DNA molecule of claim 4 wherein both said androgen responsive elements contain the conserved sequence 5'-GTTCT (SEQ ID NO: 9).

6. The DNA molecule of claim 1 wherein said at least one androgen responsive element has the sequence ATAGCATCTTGTTCTTAGT (ARE1) (SEQ ID NO: 7).

7. The DNA molecule of claim 1 wherein said at least one androgen responsive element has the sequence GTAAAGTACTCCAAGAACCTATTT (ARE2) (SEQ ID NO: 8).

8. An isolated DNA molecule comprising a 5'-flanking region of the rat probasin gene and containing at least one androgen responsive element and comprising the DNA sequence of FIG. 1 (SEQ ID NO: 1), wherein the probasin promoter region (–95 to +28 bp as shown in FIG. 1, or 332–454 bp according to Seq. Id. No.1) is replaced by a TK promoter and effective to direct expression of a heterologous gene to isolated cells.

9. An isolated DNA molecule comprising a repeated (−244 to −96 bp as shown in FIG. 1, or 182–331 bp according to Seq. Id. No.1) region of a 5'-flanking region of the rat probasin gene having the DNA sequence of FIG. 1 (SEQ ID NO: 1) linked to a TK promoter and effective to direct expression of a heterologous gene to isolated cells.

10. An isolated DNA molecule comprising at least one androgen responsive element of the 5'-flanking region of the rat probasin gene and contained within the DNA sequence shown in FIG. 1 (SEQ ID NO: 1) and effective to direct prostate-specific expression of a heterologous gene.

11. The DNA molecule of claim 10 wherein said DNA molecule comprises nucleotides −241 to −223 (ARE1) of the DNA sequence as seen in FIG. 1 (nucleotides 185–203 of SEQ ID NO: 1).

12. The DNA molecule of claim 10 wherein said DNA molecule comprises nucleotides −140 to −117 (ARE2) of the DNA sequence as seen in FIG. 1 (nucleotides 286–309 of SEQ ID NO:1).

13. An isolated DNA molecule comprising at least one androgen responsive element of the rat probasin gene and contained within the DNA sequence of FIG. 1 (SEQ ID NO: 1), said DNA molecule comprising nucleotides −140 to −117 (ARE2) as seen in FIG. 1 (nucleotides 286–309 of SEQ ID NO: 1) in which nucleotides −130 to −127 (nucleotides 296–299 of SEQ ID NO: 1) are replaced by nucleotides TACT (SEQ ID NO: 3) or GTCT (SEQ ID NO: 4) and having increased androgen activity, said DNA molecule being effective to direct expression of a heterologous gene to isolated cells.

14. An isolated DNA molecule consisting essentially of an androgen responsive fragment of the sequence of claim 2 or 3 and effective to direct expression of a heterologous gene to isolated cells.

15. The DNA molecule of claim 4 wherein one androgen responsive element has the sequence ATAGCATCTTGT-TCTTAGT (ARE1) (SEQ ID NO: 7) and the other androgen responsive element has the sequence GTAAAGTACTC-CAAGAACCTATTT (ARE2) (SEQ ID NO: 8).

16. An isolated DNA molecule comprising at least one androgen responsive element of the 5'-flanking region of the rat probasin gene and contained within the DNA sequence shown in FIG. 1 (SEQ ID No.: 1) which directs prostate-specific expression of a heterologous gene in a prostate-bearing animal under androgen regulation.

17. The DNA molecule of claim 10 wherein said DNA molecule comprises nucleotides −241 to −223 (ARE1) of the DNA sequence as seen in FIG. 1 (nucleotides 185–203 SEQ ID No.: 1) and nucleotides −140 to −117 (ARE2) of the DNA sequence as seen in FIG. 1 (nucleotides 286–309 SEQ ID No.: 1).

* * * * *

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 556 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 467..547

( x i ) SEQUENCE DESCRIPTION: SEQ ID NO: 1:

```
AAGCTTCCAC AAGTGCATTT AGCCTCTCCA GTATTGCTGA TGAATCCACA GTTCAGGTTC      60

AATGGCGTTC AAAACTTGAT CAAAAATGAC CAGACTTTAT ATTCTTACAC CAACATCTAT    120

CTGATTGGAG GAATGGATAA TAGTCATCAT GTTTAAACAT CTACCATTCC AGTTAAGAAA    180

ATATGATAGC ATCTTGTTCT TAGTCTTTTT CTTAATAGGG ACATAAAGCC CACAAATAAA    240

AATATGCCTG AAGAATGGGA CAGGCATTGG GCATTGTCCA TGCCTAGTAA AGTACTCCAA    300

GAACCTATTT GTATACTAGA TGACACAATG TCAATGTCTG TGTACAACTG CCAACTGGGA    360
```

```
TGCAAGACAC TGCCCATGCC AATCATCCTG AAAAGCAGCT ATAAAAAGCA GGAAGCTACT        420

CTGCACCTTG TCAGTGAGGT CCAGATACCT ACAGAGCTCA CACAGC ATG AGG GTC           475
                                                   Met Arg Val
                                                    1

ATC CTC CTC CTG CTC ACA CTG GAT GTG CTA GGT GTC TCC AGT ATG ATG          523
Ile Leu Leu Leu Leu Thr Leu Asp Val Leu Gly Val Ser Ser Met Met
     5                   10                  15

ACA GAC AAG AAT CTC AAA AAG AAG GTAGCAGAC                                556
Thr Asp Lys Asn Leu Lys Lys Lys
 20                  25
```

( 2 ) INFORMATION FOR SEQ ID NO: 2:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met Arg Val Ile Leu Leu Leu Leu Thr Leu Asp Val Leu Gly Val Ser
 1               5                   10                  15

Ser Met Met Thr Asp Lys Asn Leu Lys Lys Lys
             20                  25
```

( 2 ) INFORMATION FOR SEQ ID NO: 3:

( i ) SEQUENCE CHARACTERISTICS:
        ( A ) LENGTH: 4 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 3:

TACT    4

( 2 ) INFORMATION FOR SEQ ID NO: 4:

( i ) SEQUENCE CHARACTERISTICS:
        ( A ) LENGTH: 4 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 4:

GTCT    4

( 2 ) INFORMATION FOR SEQ ID NO: 5:

( i ) SEQUENCE CHARACTERISTICS:
        ( A ) LENGTH: 4 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 5:

CAAT    4

( 2 ) INFORMATION FOR SEQ ID NO: 6:

( i ) SEQUENCE CHARACTERISTICS:
  ( A ) LENGTH: 5 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO: 6:

TATAA                                                                                                 5

( 2 ) INFORMATION FOR SEQ ID NO: 7:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO: 7:

ATAGCATCTT GTTCTTAGT                                                                                  19

( 2 ) INFORMATION FOR SEQ ID NO: 8:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO: 8:

GTAAAGTACT CCAAGAACCT ATTT                                                                            24

( 2 ) INFORMATION FOR SEQ ID NO:9:

( i ) SEQUENCE CHARACTERISTICS:
  ( A ) LENGTH: 5 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:9:

GTTCT                                                                                                 5